(12) United States Patent
Winslow et al.

(10) Patent No.: US 8,070,820 B2
(45) Date of Patent: Dec. 6, 2011

(54) SHOULDER IMPLANT ASSEMBLY

(75) Inventors: Nathan A. Winslow, Warsaw, IN (US); Brian K. Berelsman, Warsaw, IN (US); Bryce A. Isch, Bluffton, IN (US); John M. McDaniel, Warsaw, IN (US); Nicholas J. Katrana, Fort Wayne, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 99 days.

(21) Appl. No.: 12/390,652

(22) Filed: Feb. 23, 2009

(65) Prior Publication Data
US 2009/0192621 A1  Jul. 30, 2009

Related U.S. Application Data

(63) Continuation-in-part of application No. 11/234,743, filed on Sep. 23, 2005, which is a continuation-in-part of application No. 10/680,924, filed on Oct. 8, 2003, now Pat. No. 7,175,663.

(51) Int. Cl.
*A61F 2/40* (2006.01)
(52) U.S. Cl. ............... 623/19.13; 623/19.11; 623/19.12
(58) Field of Classification Search .............. 623/19.11, 623/19.12, 19.13, 19.14, 23.39, 23.4, 23.44
See application file for complete search history.

(56) References Cited

U.S. PATENT DOCUMENTS

| | | | |
|---|---|---|---|
| 3,815,157 A | 6/1974 | Skorecki et al. | |
| 3,842,442 A | 10/1974 | Kolbel et al. | |
| 3,916,451 A | 11/1975 | Buechel et al. | |
| 3,978,528 A | 9/1976 | Crep | |
| 3,979,778 A | 9/1976 | Stroot | |
| 4,003,095 A | 1/1977 | Gristina | |
| 4,030,143 A | 6/1977 | Elloy et al. | |
| 4,040,131 A | 8/1977 | Gristina | |
| 4,135,517 A | 1/1979 | Reale | |
| 4,179,758 A | 12/1979 | Gristina | |
| 4,206,517 A | 6/1980 | Pappas et al. | |
| 4,693,723 A | 9/1987 | Gabard et al. | |
| 4,822,370 A | 4/1989 | Schelhas et al. | |

(Continued)

FOREIGN PATENT DOCUMENTS
DK  19509037  9/1996
(Continued)

OTHER PUBLICATIONS

Final Office Action for U.S. Appl. No. 11/234,743 Mailed Jun. 15, 2010.
(Continued)

*Primary Examiner* — David Isabella
*Assistant Examiner* — Suba Ganesan
(74) *Attorney, Agent, or Firm* — Harness, Dickey

(57) ABSTRACT

An implant assembly and associated method for selectively performing reverse and traditional arthroplasty for a shoulder joint that includes a humerus and a glenoid. The implant assembly may include a head, a cup, a humeral stem and an adaptor. The method includes inserting the humeral stem to the humerus and connecting a male taper of the adaptor to a female taper of the head. For reverse arthroplasty, the method includes attaching the adaptor to the glenoid and the cup to the stem. For traditional arthroplasty, the method includes attaching the adaptor to the humeral stem and the cup to the glenoid. The method also includes articulating the head with the cup.

13 Claims, 36 Drawing Sheets

U.S. PATENT DOCUMENTS

| | | | |
|---|---|---|---|
| 4,865,605 A | 9/1989 | Dines et al. |
| 4,865,609 A | 9/1989 | Roche |
| 4,919,670 A | 4/1990 | Dale et al. |
| 4,957,510 A | 9/1990 | Cremascoli et al. |
| 4,963,155 A | 10/1990 | Lazzeri et al. |
| 5,080,673 A | 1/1992 | Burkhead et al. |
| 5,080,685 A | 1/1992 | Bolesky et al. |
| 5,135,529 A | 8/1992 | Paxson et al. |
| 5,181,928 A | 1/1993 | Bolesky et al. |
| 5,201,882 A | 4/1993 | Paxson |
| 5,222,984 A | 6/1993 | Forte |
| 5,314,479 A | 5/1994 | Rockwood, Jr. et al. |
| 5,358,526 A | 10/1994 | Tornier et al. |
| 5,462,563 A | 10/1995 | Shearer et al. |
| 5,507,817 A | 4/1996 | Craig et al. |
| 5,507,818 A | 4/1996 | McLaughlin |
| 5,507,824 A | 4/1996 | Lennox |
| 5,549,682 A | 8/1996 | Roy |
| 5,580,352 A | 12/1996 | Sekel et al. |
| 5,702,457 A | 12/1997 | Walch et al. |
| 5,702,486 A | 12/1997 | Craig et al. |
| 5,723,018 A | 3/1998 | Cyprien et al. |
| 5,728,161 A | 3/1998 | Camino et al. |
| 5,902,340 A | 5/1999 | White et al. |
| 5,910,171 A | 6/1999 | Kummer et al. |
| 5,961,555 A | 10/1999 | Huebner |
| 6,033,439 A | 3/2000 | Camino et al. |
| 6,045,582 A | 4/2000 | Prybyla |
| 6,102,953 A | 8/2000 | Huebner |
| 6,129,764 A | 10/2000 | Servidio |
| 6,171,341 B1 | 1/2001 | Boileau et al. |
| 6,197,062 B1 | 3/2001 | Fenlin |
| 6,197,063 B1 | 3/2001 | Dews et al. |
| 6,206,925 B1 | 3/2001 | Tornier et al. |
| 6,228,120 B1 | 5/2001 | Leonard et al. |
| 6,364,910 B1 | 4/2002 | Shultz et al. |
| 6,368,352 B1 | 4/2002 | Camino et al. |
| 6,620,197 B2 | 9/2003 | Maroney et al. |
| 6,626,946 B1 | 9/2003 | Walch et al. |
| 6,719,799 B1 | 4/2004 | Kropf et al. |
| 6,761,740 B2 | 7/2004 | Tornier et al. |
| 6,790,234 B1 | 9/2004 | Frankle |
| 6,890,358 B2 * | 5/2005 | Ball et al. ............ 623/21.13 |
| 6,942,699 B2 | 9/2005 | Stone et al. |
| 6,974,483 B2 | 12/2005 | Murray |
| 6,986,790 B2 | 1/2006 | Ball et al. |
| 7,022,141 B2 | 4/2006 | Dwyer et al. |
| 7,097,663 B1 | 8/2006 | Nicol et al. |
| 7,135,044 B2 | 11/2006 | Bassik et al. |
| 7,175,663 B1 | 2/2007 | Stone |
| 7,189,261 B2 | 3/2007 | Dews et al. |
| 7,238,207 B2 | 7/2007 | Blatter et al. |
| 7,819,923 B2 | 10/2010 | Stone et al. |
| 2001/0049561 A1 | 12/2001 | Dews et al. |
| 2001/0053935 A1 | 12/2001 | Hartdegen et al. |
| 2002/0120339 A1 | 8/2002 | Callaway et al. |
| 2002/0138148 A1 | 9/2002 | Hyde |
| 2002/0156534 A1 | 10/2002 | Grusin et al. |
| 2003/0028253 A1 | 2/2003 | Stone et al. |
| 2003/0097183 A1 | 5/2003 | Rauscher et al. |
| 2003/0114933 A1 | 6/2003 | Bouttens et al. |
| 2003/0158605 A1 | 8/2003 | Tornier |
| 2004/0064189 A1 | 4/2004 | Maroney et al. |
| 2004/0064190 A1 | 4/2004 | Ball et al. |
| 2004/0220673 A1 | 11/2004 | Pria |
| 2004/0220674 A1 | 11/2004 | Pria |
| 2005/0197708 A1 | 9/2005 | Stone et al. |
| 2006/0020344 A1 | 1/2006 | Shultz et al. |
| 2007/0142918 A1 | 6/2007 | Stone |
| 2007/0198094 A1 | 8/2007 | Berelsman et al. |
| 2009/0210065 A1 | 8/2009 | Nerot et al. |
| 2009/0270993 A1 | 10/2009 | Maisonneuve et al. |
| 2011/0035013 A1 | 2/2011 | Winslow et al. |
| 2011/0035015 A1 | 2/2011 | Stone et al. |
| 2011/0054624 A1 | 3/2011 | Iannotti |
| 2011/0118846 A1 | 5/2011 | Katrana et al. |

FOREIGN PATENT DOCUMENTS

| | | |
|---|---|---|
| EP | 0257359 | 3/1988 |
| EP | 0599429 | 6/1994 |
| EP | 0664108 | 7/1995 |
| EP | 0679375 | 11/1995 |
| EP | 0712617 | 5/1996 |
| EP | 0797964 | 10/1997 |
| EP | 1472999 | 11/2004 |
| EP | 1520560 | 4/2005 |
| EP | 1639965 | 3/2006 |
| FR | 2574283 | 6/1986 |
| FR | 2652498 | 4/1991 |
| FR | 2664809 | 1/1992 |
| FR | 2704747 | 11/1994 |
| FR | 2721200 | 12/1995 |
| FR | 2848099 | 6/2004 |
| FR | 2852229 | 9/2004 |
| GB | 2405346 | 3/2005 |
| WO | WO 9522302 | 8/1995 |
| WO | WO-9617553 | 6/1996 |
| WO | WO-9846172 | 10/1998 |
| WO | WO-0015154 | 3/2000 |

OTHER PUBLICATIONS

Non-Final Office Action for U.S. Appl. No. 11/234,743 Mailed Dec. 2, 2009.

Non-Final Office Action for U.S. Appl. No. 11/234,743 Mailed Dec. 21, 2010.

Non-Final Office Action for U.S. Appl. No. 12/911,238 Mailed Jul. 1, 2011.

"Buechel-Pappas.TM. Total Shoulder System", Endotec, Jul. 1991.

"Delta Prothese Totale D'epaule Inversee", Depuy (8 sheets). cited by other, submitted Oct. 2004.

"Reverse Shoulder Prosthesis", Encore Surgical (2 sheets). cited by other, submitted Oct. 2004.

Surgery Eases Rotator Cuff Pain by Ruth Campbell Odessa American, online article, (2 sheets) dated Feb. 9, 2005.

Thabe et al., "Die endoprothetische Versorgung des rheumatischen Schultergelenkes", Aktuelle Rheumatologie, vol. 19 (1994), pp. 155-160 (with English abstract).

Thabe et al., "Modulares—Vario—Schulter", 6 sheets of pictures, cited Oct. 2004.

The Delta CTA™ Reverse Shoulder System, copyright Johnson & Johnson Gateway LLC 2000-2005 online article (2 sheets) dated Feb. 9, 2005.

* cited by examiner

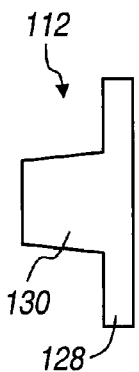 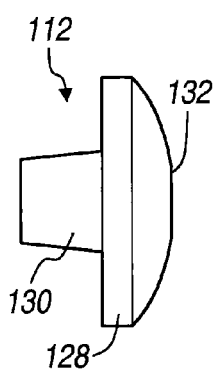 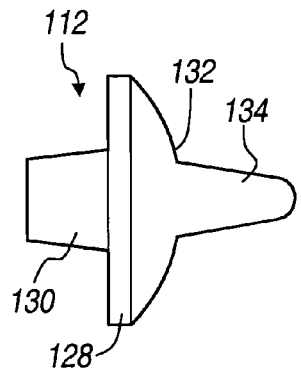 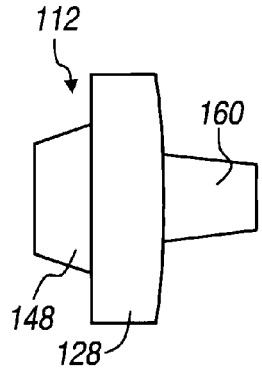
FIG. 3A    FIG. 3B    FIG. 3C    FIG. 3D
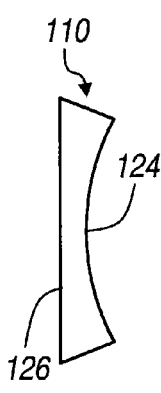 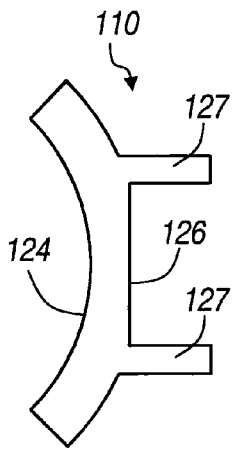 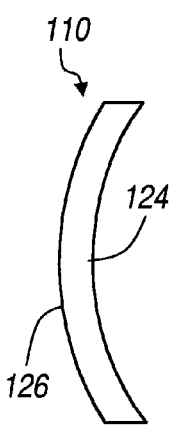 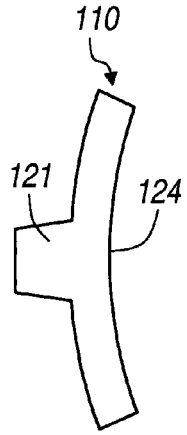
FIG. 4A    FIG. 4B    FIG. 4C    FIG. 4D
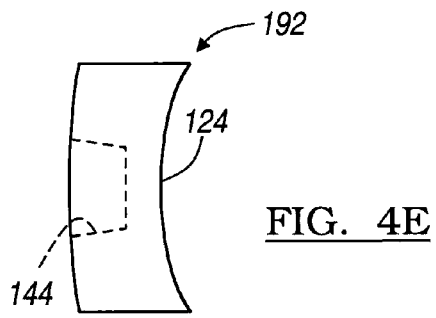
FIG. 4E

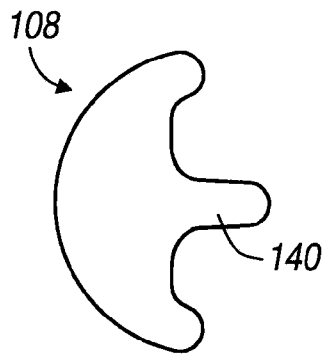
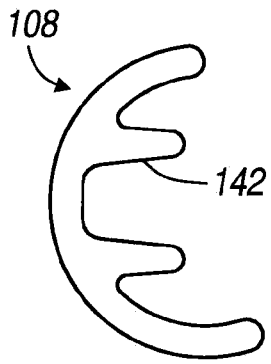
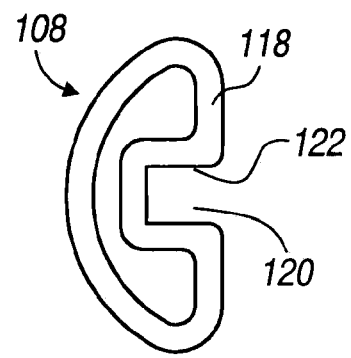
FIG. 9A          FIG. 9B          FIG. 9C
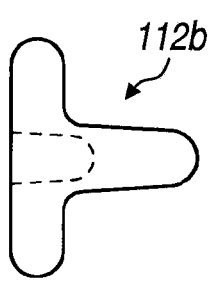
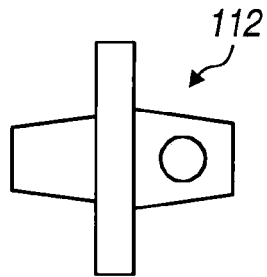
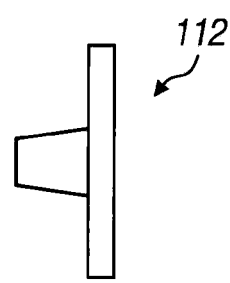
FIG. 10A         FIG. 10B         FIG. 10C
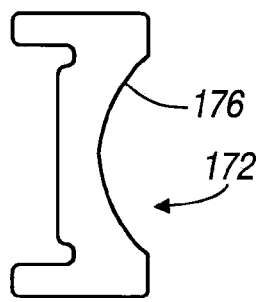
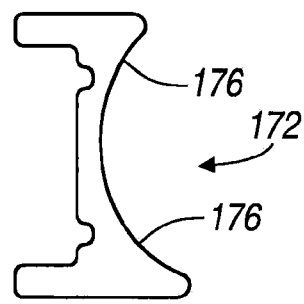
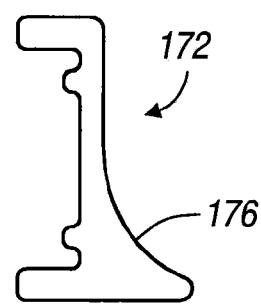
FIG. 11A         FIG. 11B         FIG. 11C

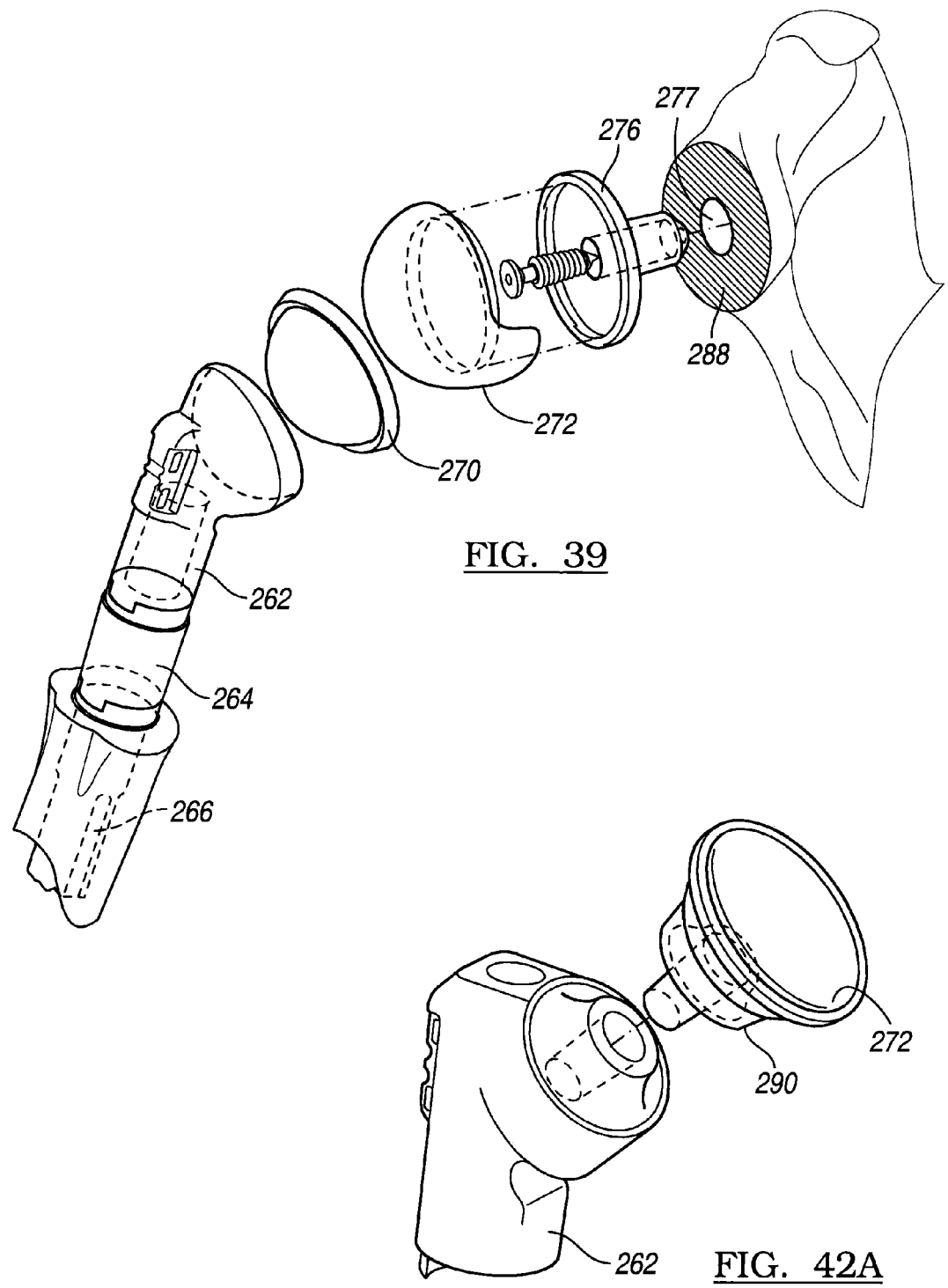

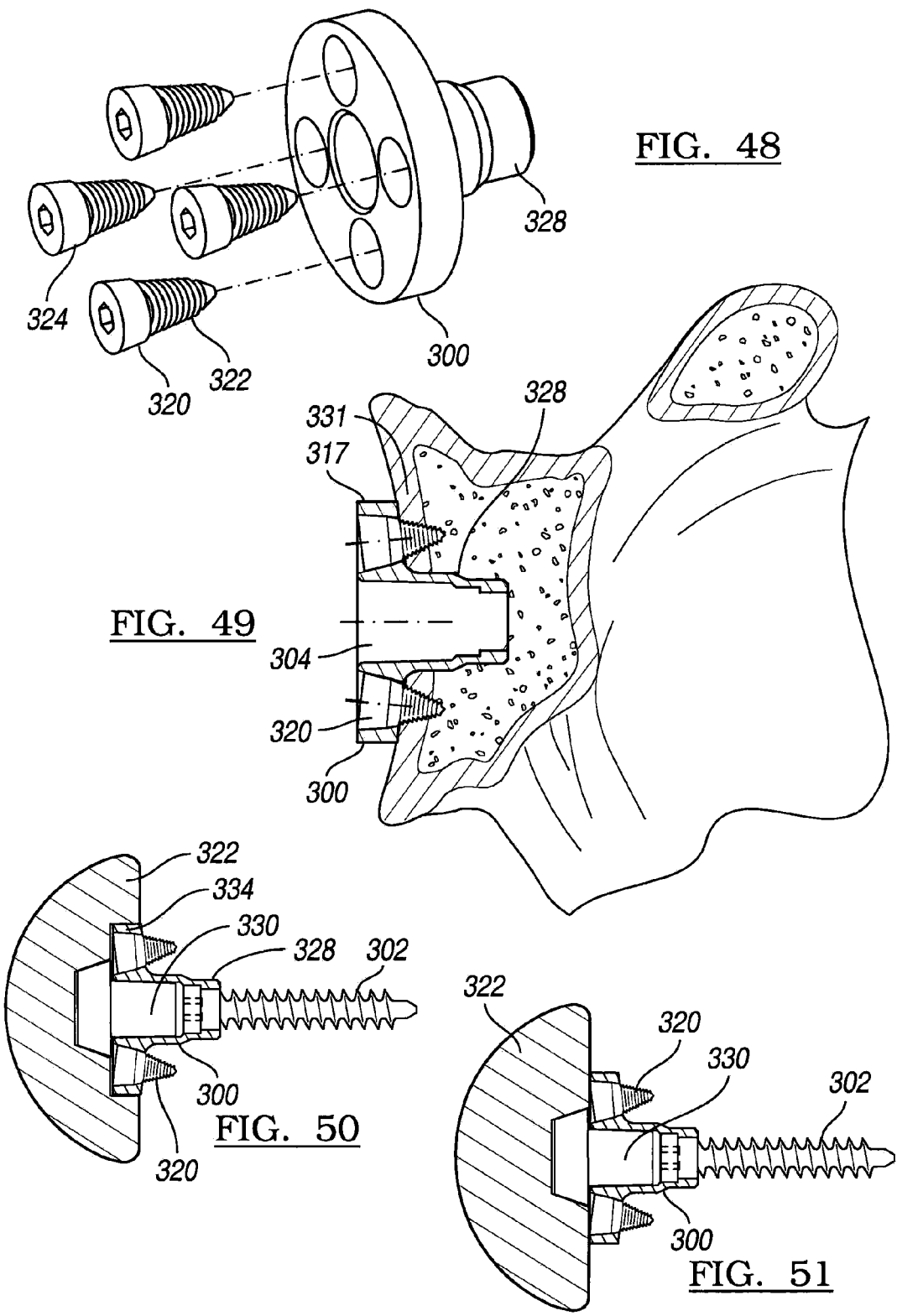

SHOULDER IMPLANT ASSEMBLY

CROSS-REFERENCE TO RELATED APPLICATIONS

This application is a continuation-in-part application of U.S. patent application Ser. No. 11/234,743 filed on Sep. 23, 2005, which is a continuation-in-part of U.S. patent application Ser. No. 10/680,924 filed on Oct. 8, 2003 and issued Feb. 13, 2007 as U.S. Pat. No. 7,175,663. The disclosure of the above applications is incorporated herein by reference.

FIELD OF THE INVENTION

The present invention relates to an implant assembly for shoulder joint replacement.

BACKGROUND OF THE INVENTION

A natural shoulder joint may undergo degenerative changes caused by a variety of reasons. When these degenerative changes become so far advanced and irreversible, it may ultimately become necessary to replace a natural shoulder joint with a prosthetic shoulder joint. In the traditional implantation of a shoulder joint prosthesis, the natural head portion of the humerus is resected and a cavity is created in the intramedullary canal of the host humerus for accepting a humeral component. The humeral component generally includes a stem and a head portion, which is used to replace the natural head of the humerus. Once the humeral component has been implanted, the glenoid cavity positioned at the scapula may also be resected and shaped to accept a glenoid component. The glenoid component generally includes an articulating surface or cup which is engaged by the head portion of the humeral component. Modular designs for the humeral and glenoid components are currently available for the traditional shoulder arthroplasty, and components of different sizes or shapes are at the disposal of the surgeon performing the operation.

The traditional shoulder joint arthroplasty typically involves the coupling of a humeral head with a modified humerus, while a concave bearing member can be placed on a prepared glenoid. In the reverse shoulder prosthesis, the humeral component includes a stem and a cup connected to the stem. The glenoid component supports a head which articulates with the cup.

It is not always practical to determine well in advance of the procedure whether a reverse or traditional shoulder prosthesis should be used. It is, therefore, desirable to provide a selection of modular components that can be combined for use in traditional as well as reverse shoulder arthroplasty, with the goals of increasing flexibility and choice and for providing interchangeable and easy to use components that are also cost effective.

SUMMARY OF THE INVENTION

One embodiment of the invention provides an implant assembly for a shoulder joint that has a humerus and a glenoid. The implant assembly may include a humeral stem configured to be inserted in the humerus, and a head bounded by a convex surface and a planar base that has a female taper. The implant assembly also includes an adaptor having a tray and a male taper. The tray may be configured to be attached to the glenoid. The male taper of the adaptor is configured to be received in the female taper of the head. The implant assembly also includes a cup that can be attached to the stem. The cup has a concave surface that is configured to articulate with the convex surface of the head.

Another embodiment of the invention provides an assembly of implant components for a shoulder joint having a humerus and a glenoid. The assembly includes a humeral stem, a head having a convex surface, and a cup configured to articulate with the convex surface of the head. The assembly optionally includes a glenoid adaptor for a reverse shoulder arthroplasty, and a humeral adaptor for traditional shoulder arthroplasty. The glenoid adaptor is configured to connect the head to the glenoid when the cup is connected to the humeral stem. The optional humeral adaptor is configured to connect the head to the humeral stem when the cup is connected to the glenoid. The same adaptor may be used as a glenoid and as a humeral adaptor.

Another embodiment of the invention provides an assembly of implant components for a shoulder joint having a humerus and a glenoid. The assembly includes a plurality of humeral stems, a plurality of heads, and a plurality of cups configured to articulate with the heads. The assembly also includes a plurality of glenoid adaptors for a reverse shoulder arthroplasty, and a plurality of humeral adaptors for traditional shoulder arthroplasty. The humeral or glenoid adaptors have an offset feature which allows for relative positioning of the humeral or glenoid articulating surfaces. Each glenoid adaptor is configured to connect one of the heads to the glenoid when one of the cups is connected to one of the humeral stems. Each humeral adaptor is configured to connect one of the heads to one of the humeral stems when one of the cups is connected to the glenoid.

Another embodiment provides a method for selectively performing reverse and traditional arthroplasty for a shoulder joint that includes a humerus and a glenoid. The method includes providing a head, a cup, and a humeral stem. The method also includes providing a humeral adaptor for traditional arthroplasty, and providing a glenoid adaptor for reverse arthroplasty. Further, the method includes selecting one of the humeral and glenoid adaptors, and performing the corresponding arthroplasty utilizing the head, the cup, the humeral stem and the selected adaptor.

Another embodiment provides a method for selectively performing reverse and traditional arthroplasty for a shoulder joint that includes a humerus and a glenoid. The method includes inserting a humeral stem to the humerus and connecting an adaptor to a head with mating male and female tapers. The method also includes selectively attaching a base of the adaptor to the glenoid for reverse arthroplasty and to the stem for traditional arthroplasty, and selectively attaching a cup to the stem for reverse arthroplasty, and to the glenoid for traditional arthroplasty. Further, the method includes articulating the head with the cup.

Further areas of applicability of the present invention will become apparent from the detailed description provided hereinafter. It should be understood that the detailed description and specific examples, while indicating current embodiments of the invention, are intended for purposes of illustration only and are not intended to limit the scope of the invention.

BRIEF DESCRIPTION OF THE DRAWINGS

The present invention will become more fully understood from the detailed description and the accompanying drawings. The components in the drawings are not necessarily to scale, emphasis instead being placed upon illustrating the principles of the invention.

FIGS. 3A-3D are side views of embodiments of an adaptor according to the present invention;

FIGS. 4A-4E are side views of embodiments of a cup according to the present invention;

FIGS. 9A-9C are side views of embodiments of heads according to the invention;

FIGS. 10A-10C are side views of embodiments of adaptors corresponding to the heads of FIGS. 9A-9C;

FIGS. 11A-11C are side views of embodiments of head bearings;

FIGS. 36-40 represent an implant shown in FIG. 35 utilizing an alternate head;

FIGS. 42A and 42B represent a humeral body portion shown in FIGS. 35-40.

FIGS. 48 and 49 represent an alternate method to fix the tray of FIG. 43 to a prepared glenoid;

FIGS. 50 and 51 represent alternate mechanisms to couple a head to the tray of FIG. 43;

DETAILED DESCRIPTION OF THE PREFERRED EMBODIMENTS

The following description of the preferred embodiments of the invention is merely exemplary in nature and is in no way intended to limit the invention, its application, or uses.

Figure 1:
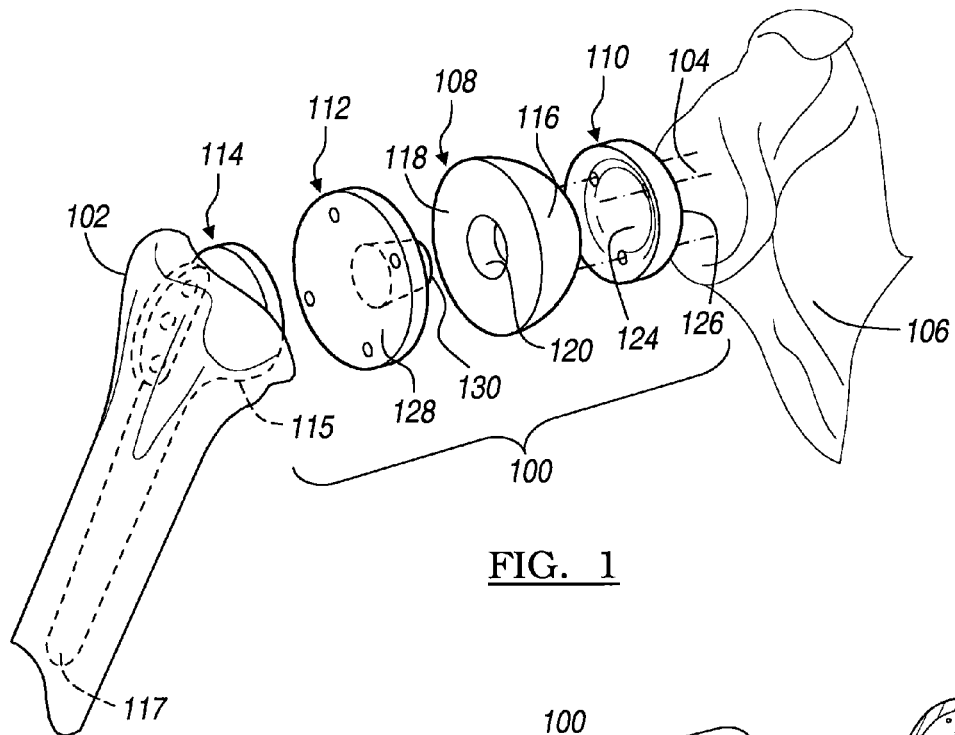
FIG. 1 is an exploded view of an embodiment of an implant assembly according to the invention, shown in a traditional shoulder arthroplasty.
Figure 2:
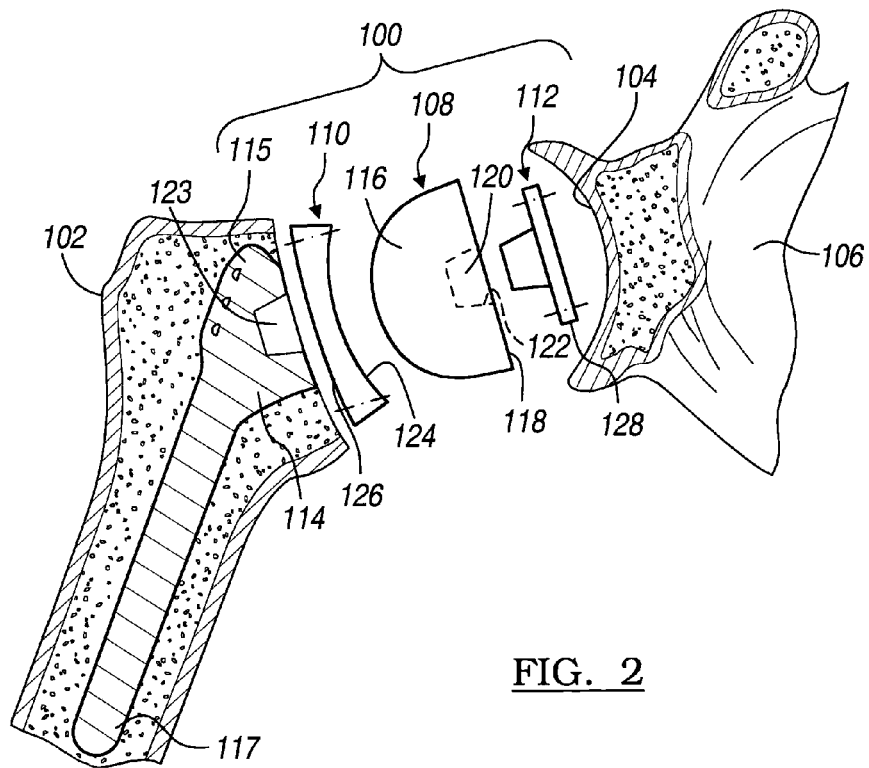
FIG. 2 is an exploded view of an embodiment of an implant assembly according to the invention, shown in a reverse shoulder arthroplasty.

Referring to FIGS. 1 and 2, there is shown an embodiment of an implant assembly 100 for a total shoulder joint replacement. The implant assembly 100 is configured to be implanted between a resected humerus 102 and a glenoid cavity ("glenoid") 104 of a scapula 106 in one of two ways, i.e., in a traditional arthroplasty depicted in FIG. 1, or in a reverse arthroplasty depicted in FIG. 2, by selecting and/or reconfiguring appropriately the components of the implant assembly 100. The implant assembly 100 includes a head 108, a cup 110, and an adaptor 112. The implant assembly 100 may also include a humeral stem 114 that has a proximal end 115 and a distal end 117.

Figure 5A:
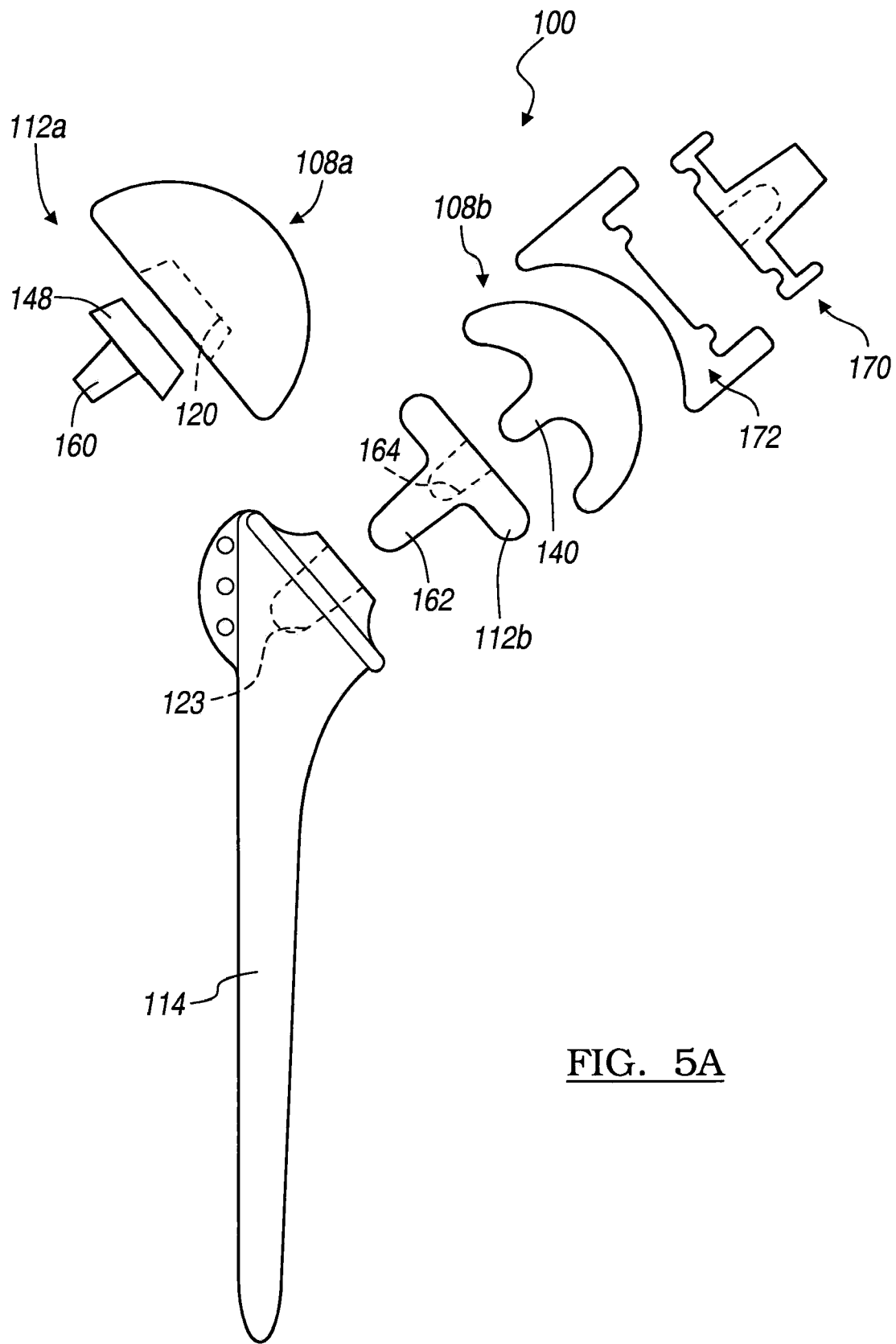
FIG. 5A is an exploded view of an embodiment of an implant assembly according to the invention, shown in a traditional shoulder arthroplasty and with alternative heads and humeral adaptors.
Figure 15:
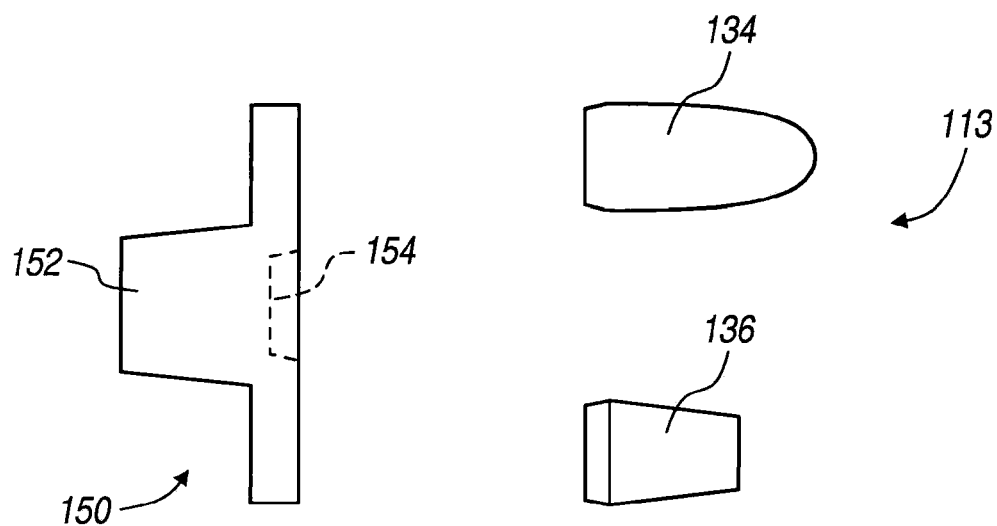
FIG. 15 is an exploded view of an embodiment of modular adaptor, shown with glenoid and humeral stems.
Figure 16:
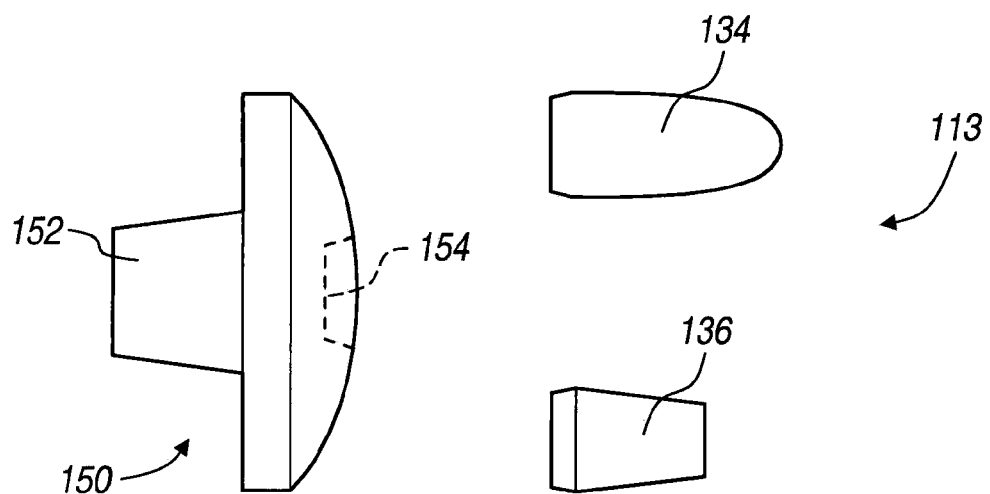
FIG. 16 is an exploded view of an embodiment of modular adaptor, shown with glenoid and humeral stems.

Other embodiments of the implant assembly are shown in FIGS. 5A, 6A, 12, and 13 for traditional shoulder replacement, and in FIGS. 5B, 6B, 7 and 14 for reverse shoulder replacement. FIGS. 3A-3D, 4A-4E, 9A-9C, 10A-10C, and 11A-11C show representative embodiments of various components. FIGS. 15 and 16 show embodiments of a modular adaptor 113. FIG. 8 shows an embodiment of a component assembly (kit) for shoulder replacement 800 showing different sizes of representative components. It should be understood that the component assembly 800 in FIG. 8 is only illustrative of the inclusion of different sizes of each component and it is not limited by the type of components actually shown. For example, the component assembly 800 may include different sizes of each of the heads 108 shown in FIGS. 9A-9C, different types and sizes of adaptors 112, different sizes and types of cups 110, etc. Like reference numerals refer to like components. When clarity requires differentiating between different embodiments of the same component, an alphabetic character is attached to the reference numeral. For example, the head 108 is referenced as head 108A and head 108B to distinguish between two different head embodiments, as shown in FIG. 5A.

In the embodiment shown in FIGS. 1 and 2, the head 108 is bounded by a convex surface 116, which may be, for example, a hemispherical surface, and a base 118, which may be a substantially planar surface. In one embodiment, the base 118 may be modularly connected to the head 108. A female taper 120 with tapered inner walls 122 extends from the base 118 into the head 108. The convex surface 116 of the head 108 is shaped to articulate with a concave surface 124 of the cup 110 to allow for shoulder joint movement. Such articulation may be centered or eccentric. This and other embodiments of the head 108 are shown in FIGS. 9A-9C. In the embodiment of FIG. 9A, the head 108 has a male taper 140. In the embodiment of FIG. 9B, the head 108 has a female taper 142.

Referring to FIGS. 1 and 2, the cup 110 may include a back surface 126 that may be configured to be selectively attached to the humeral stem 114 in reverse shoulder arthroplasty, or to the resected glenoid 104 in the traditional shoulder arthroplasty. Alternatively, the cup 110 may be chosen from a number for available cups, such as those shown in FIGS. 4A-4D, some of which are better suited to either reverse shoulder arthroplasty or traditional shoulder arthroplasty. For example, the back surface 126 of the cup 110 may be a substantially planar surface which can be attached with cement or with mechanical fasteners, such as screws, to the humeral stem 114 or to the appropriately resected glenoid 104. Alternatively, as shown in FIG. 4C, the back surface 126 may be slightly convex. In the embodiment shown in FIG. 4B, the back surface 126 may include a number of pegs 127 for attachment to the glenoid 104. In the embodiment shown in FIG. 4D, the cup 110 may include a male taper 121 which is received in a corresponding female taper 123 of the proximal end 115 of the humeral stem 114. FIG. 4E shows a bearing 192 of a modular cup 110 that has a concave surface 124 and a female taper 144 adapted to receive a modular glenoid stem 130 or modular humeral stem 136, such as those shown in FIGS. 15 and 16 in connection with the modular adaptor 113. The bearing 192 may also be used with the embodiments of FIGS. 13 and 14, as is described below.

Referring to FIGS. 15 and 16, the modular adaptor 113 may include a body 150 with a male taper 152 and a female taper 154. The female taper 154 is adapted to receive a glenoid stem 134 for the reverse shoulder arthroplasty and a humeral stem 136 for the traditional shoulder arthroplasty. The male taper 152 is adapted to be received in the female taper 142 of the embodiment of the head 108 shown in FIG. 9B or in the female taper 120 of the embodiment of the head 108 shown in FIG. 9C, for example.

In general, the adaptor 112 may be modular, such as the adaptor 113 of FIGS. 15 and 16, or a monolithic adaptor. The adaptor 112 may be a single, one and the same, adaptor that can be used selectively in both the traditional and the reverse shoulder arthroplasty, or it can be chosen from a number of available adaptors of an assembly of components, such as those shown in FIGS. 3A-3D, depending on which arthroplasty procedure is to be performed. Some of these adaptors 112, such as, for example, the adaptor shown in FIG. 3C, may be specifically configured for use with reverse arthroplasty, because they incorporate the glenoid stem 134, either modularly or monolithically.

In one embodiment, the adaptor 112 may include an adaptor tray 128 and an extension or male taper 130 that can be press-fitted into the female taper 120 of the head 108. For the procedure of traditional shoulder arthroplasty, the tray 128 is attached to the proximal end of the humeral stem 114, as shown in FIG. 1. For the procedure of reverse arthroplasty, the tray 128 is attached to the glenoid 104, as shown in FIG. 2. In the embodiments of FIGS. 3A and 3C, the tray 128 may include a curved portion 132 shaped to conform to a portion of the glenoid 104. It may also include the glenoid stem 134, which is inserted into the glenoid 104. The adaptor may be attached to the glenoid 104 with fasteners, such as screws.

Referring to the embodiment of FIG. 3A, the tray 128 may also be substantially planar. It will be appreciated, however, that other shapes, in addition to those shown in FIGS. 3A-3D, are possible for the tray 128 depending, for example, on the various ways the tray 128 is be attached to the humerus 102, to the humeral stem 114, or to the glenoid 104. Furthermore, the adaptor 112 may be modular, such that the male taper 130, the tray 128 and the glenoid stem 134 are all separate components interconnected though fasteners, such as screws, or other type of connectors, including male-female tapers as illustrated in FIGS. 15 and 16. The adaptors 112, 112A shown in FIGS. 3D and 5A include a male taper 148 which can be received in the female taper of 120 of the head 108, 108A, and a male taper 160 which can be received in the female taper 123 of the humeral stem 114.

Figure 5B:
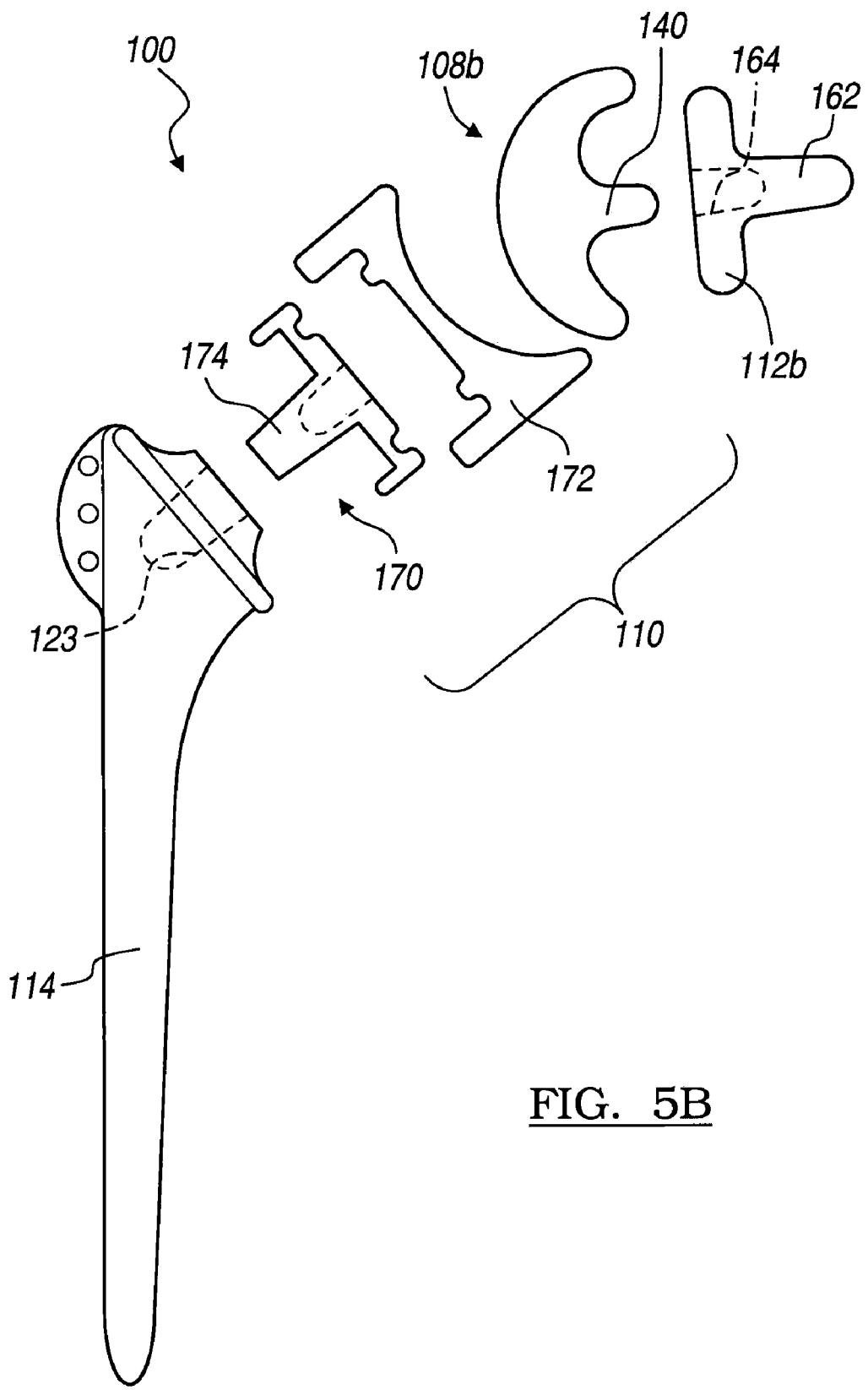
FIG. 5B is an exploded view of an embodiment of an implant assembly according to the invention, shown in a reverse shoulder arthroplasty.
Figures 6A, 6B:
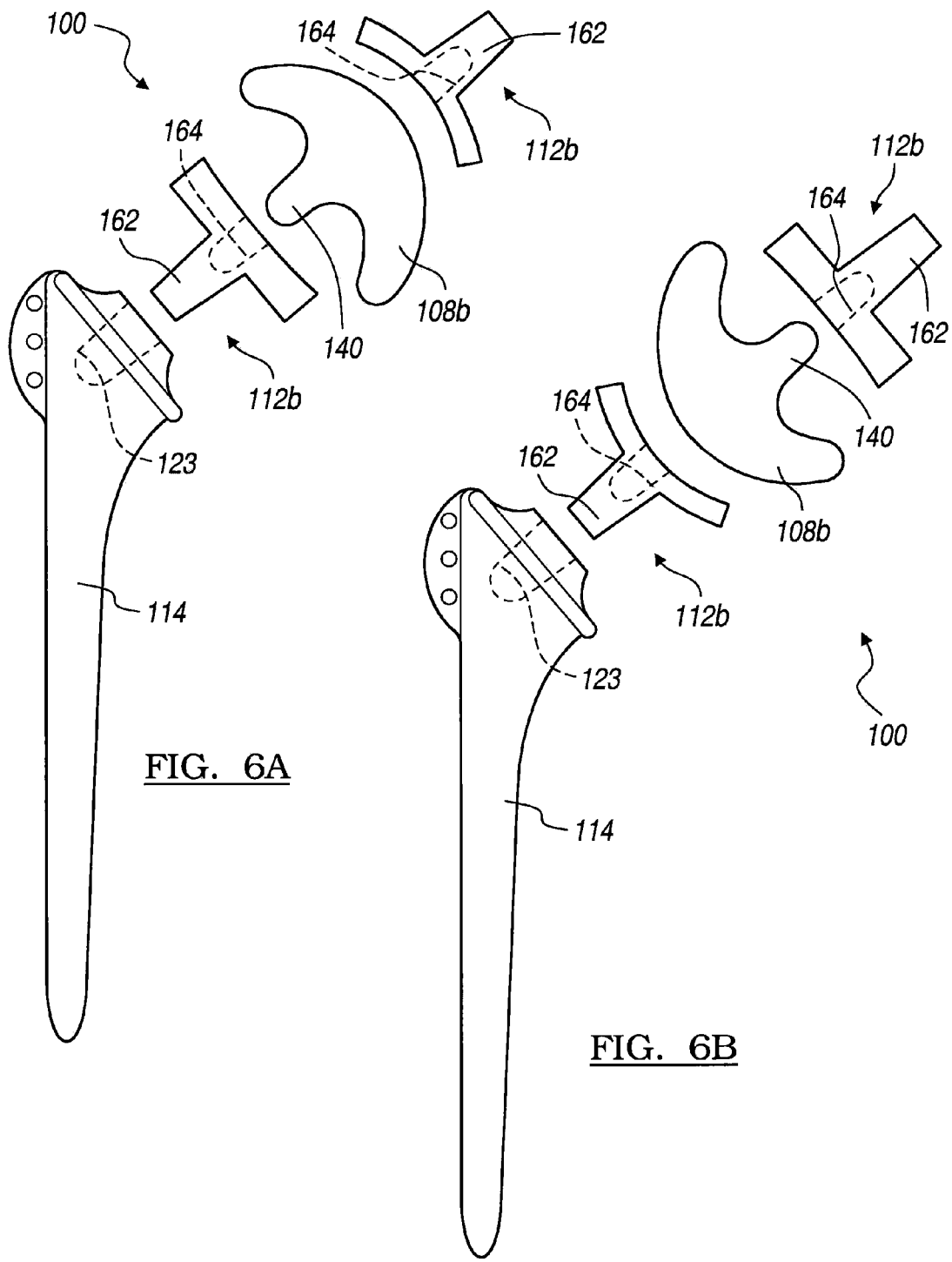
FIG. 6A is an exploded view of an embodiment of an implant assembly according to the invention, shown in a traditional shoulder arthroplasty.
FIG. 6B is an exploded view of an embodiment of an implant assembly according to the invention, shown in a reverse shoulder arthroplasty.
Figure 7:
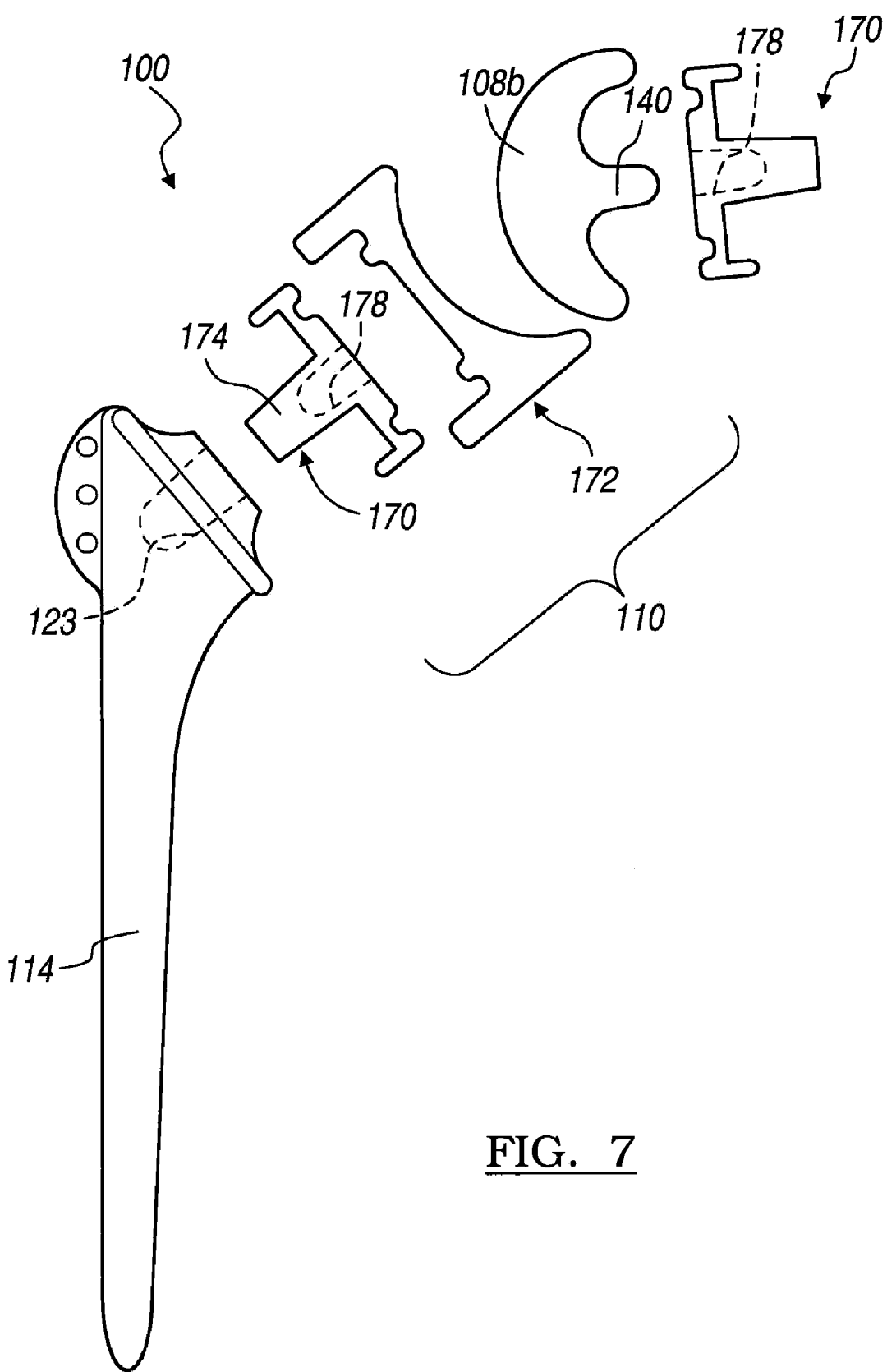
FIG. 7 is an exploded view of an embodiment of an implant assembly according to the invention, shown in a reverse shoulder arthroplasty.
Figure 8:
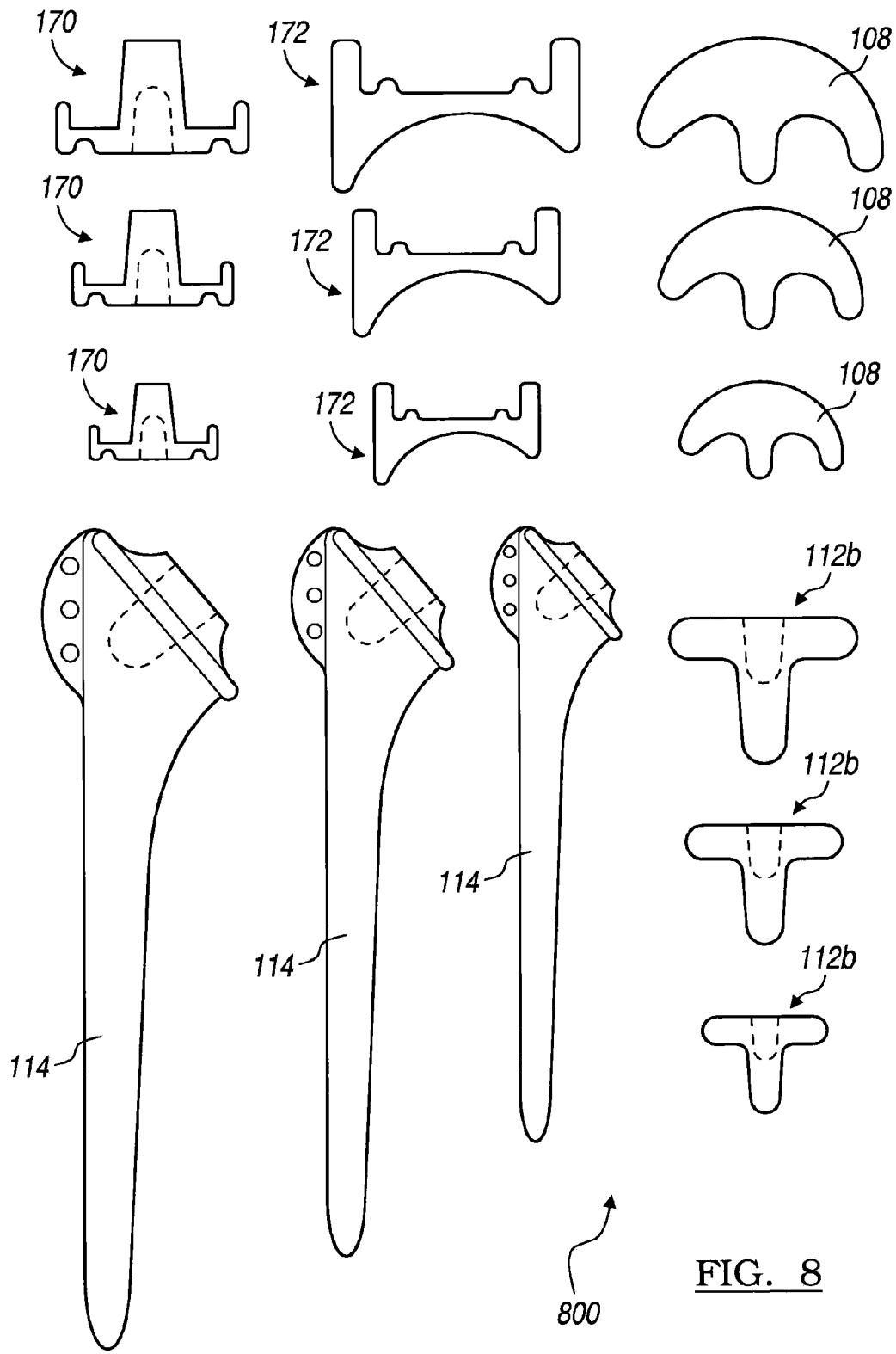
FIG. 8 is an embodiment of a assembly of components for shoulder arthroplasty according to the invention.

In the embodiments illustrated in FIGS. 5B and 7, the cup 110 may be replaced by a bearing base 170, which is also an adaptor, and a bearing 172 that can be fitted to the base 170. The bearing base 170 has a male taper 174 configured to be received in the female taper 123 of the humeral stem 114. Examples of bearings 172 with symmetric or non-symmetric and eccentric bearing surfaces 176 are shown in FIGS. 11A-11C. In the embodiment of FIG. 7, the bearing base 170, includes a female taper 178 adapted to receive the male taper 140 of the head 108B.

Figure 12:
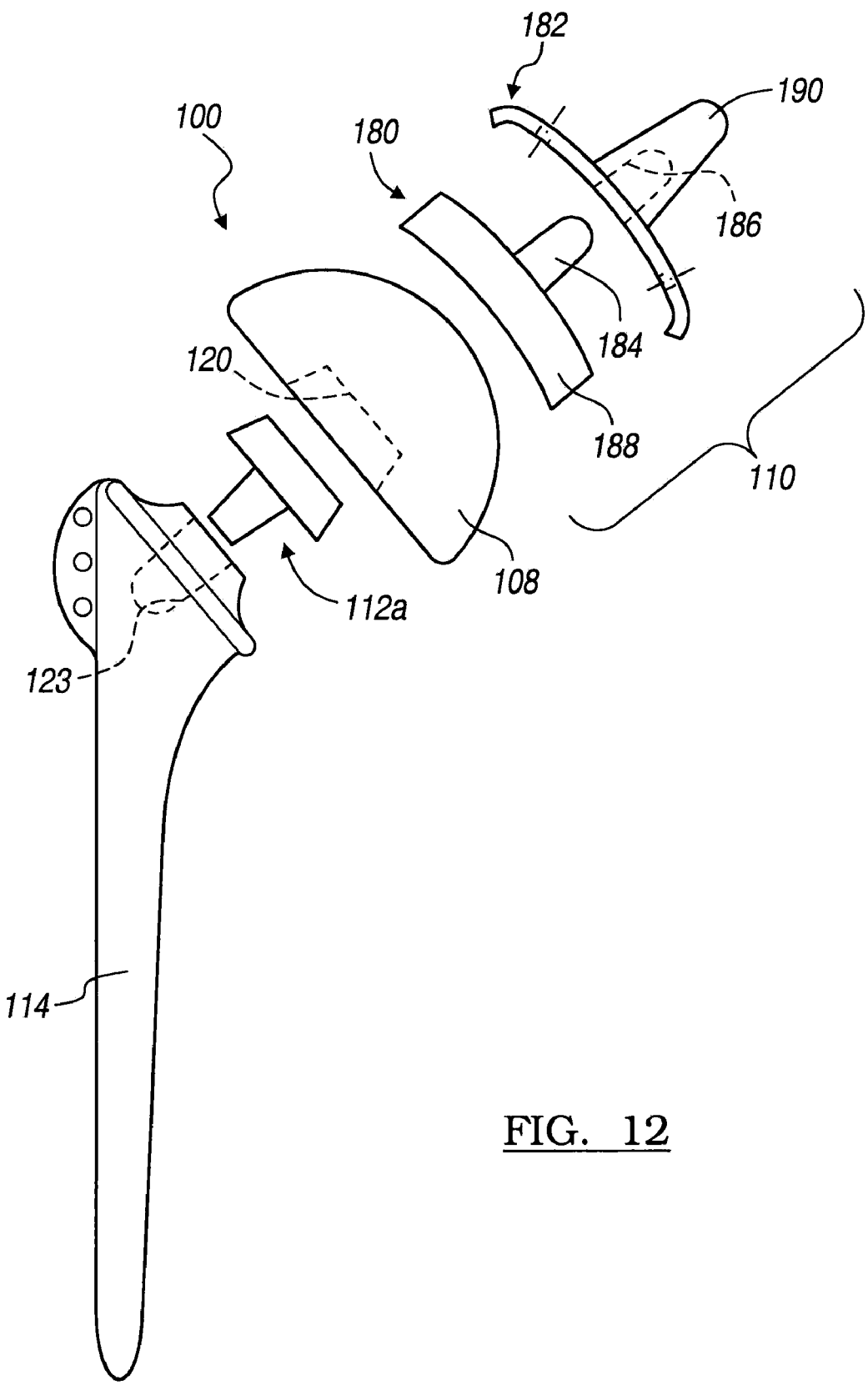
FIG. 12 is an exploded view of an embodiment of an implant assembly according to the invention, shown in a traditional shoulder arthroplasty.

In the embodiment of FIG. 12, the cup 110 may be replaced by a bearing 180 that is fitted in a bearing base 182 with mating male taper 184 and female taper 186, or with a bearing 180 that includes only a liner 188. The bearing base 182 may include a modular or integral glenoid stem 190.

Referring to FIGS. 1 and 2, for example, the implant assembly 100 may be used as follows. The humeral stem 114 is inserted in the resected humerus 102. The adaptor 112 is attached to the head 108 by inserting the male taper 130 into the female taper 120. For traditional shoulder arthroplasty, the cup 110 is attached to the glenoid 104, and the adaptor 112 is attached to the proximal end 115 of the humeral stem 114, such that the convex surface 116 of head 108 articulates with the concave surface 124 of the cup 110. For reverse shoulder arthroplasty, the cup 110 is attached to the proximal end 115 of the stem humeral 114 and the adaptor 112 is attached to the resected glenoid 104 such that the convex surface 116 of head 108 articulates with the concave surface 124 of the cup 110. Although the same adaptor 112 can be used for both the traditional and the reverse shoulder arthroplasty procedures, glenoid-specific adaptors 112 may be chosen, either as integral components or built from modular parts that include male tapers 130, trays 128 and glenoid stems 134.

It will be appreciated that the individual components of the implant assembly 100 may be made using a variety of materials, including metal and plastic. The head and the stem may be made of metallic material, such as a cobalt chrome alloy, for example. Porous coating may be provided for the proximal end of the stem. The cup may be made of polyethylene or metal or a combination thereof, such as polyethylene bearing or lining and metal base. The adaptor can be typically made of metal.

Other exemplary embodiments are illustrated in FIGS. 5A, 5B, 6A, 6B, 7, and 12-14. In FIG. 5A, the male taper 140 of the head 108B can also be inserted directly into the female taper 123 of the humeral stem 123. Alternatively, an adaptor 112B having a male taper 162 and a female taper 164 may be provided. The adaptor 112B may be also used in the embodiments shown in FIGS. 5B, 6A, and 6B.

Figure 13:
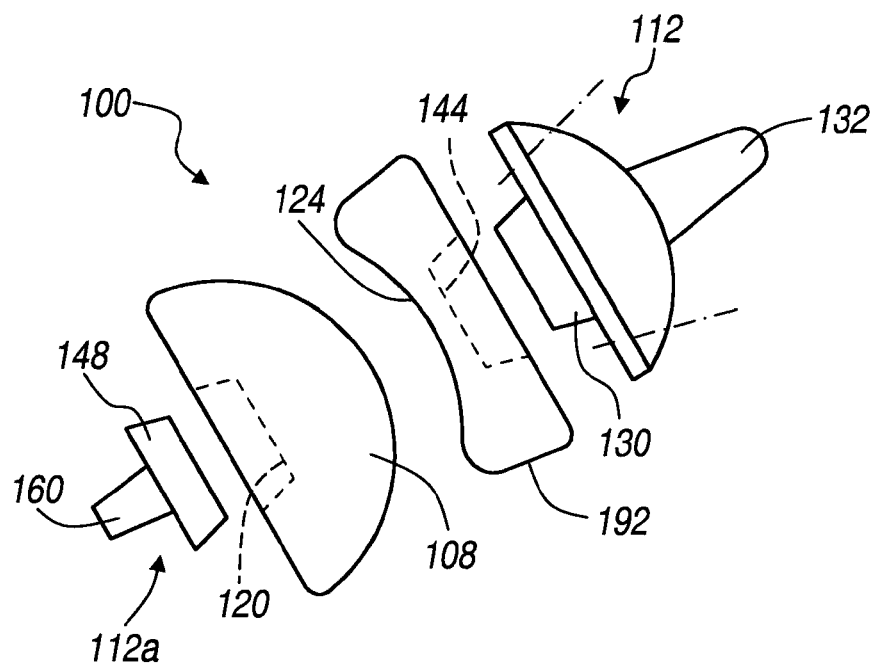
FIG. 13 is an exploded view of an embodiment of an implant assembly according to the invention, shown in a traditional shoulder arthroplasty without a humeral stem.
Figure 14:
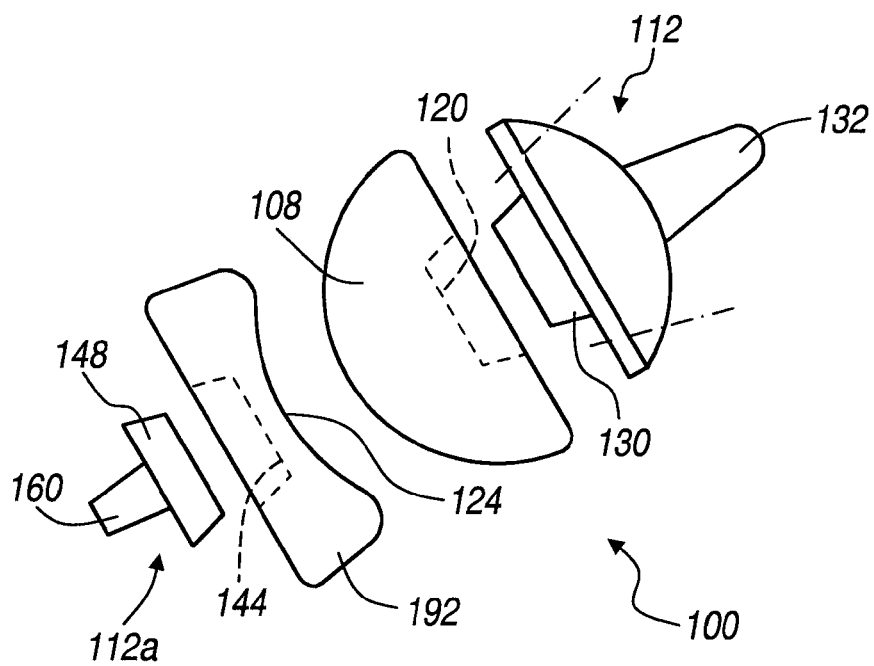
FIG. 14 is an exploded view of an embodiment of an implant assembly according to the invention, shown in a reverse shoulder arthroplasty without a humeral stem.

In the embodiments of FIGS. 13 and 14, the male taper 148 of the adaptor 112A can be received in the female taper 120 of the head 108 for the traditional shoulder arthroplasty shown in FIG. 13, and in the female taper 144 of the bearing 192 for the reverse arthroplasty shown in FIG. 14. Similarly, the male taper 130 of the glenoid adaptor 112 may be received in the female taper 120 of the head 108 for the reverse shoulder arthroplasty, and in the female taper 144 of the bearing 192 for the traditional shoulder arthroplasty.

Figure 17:
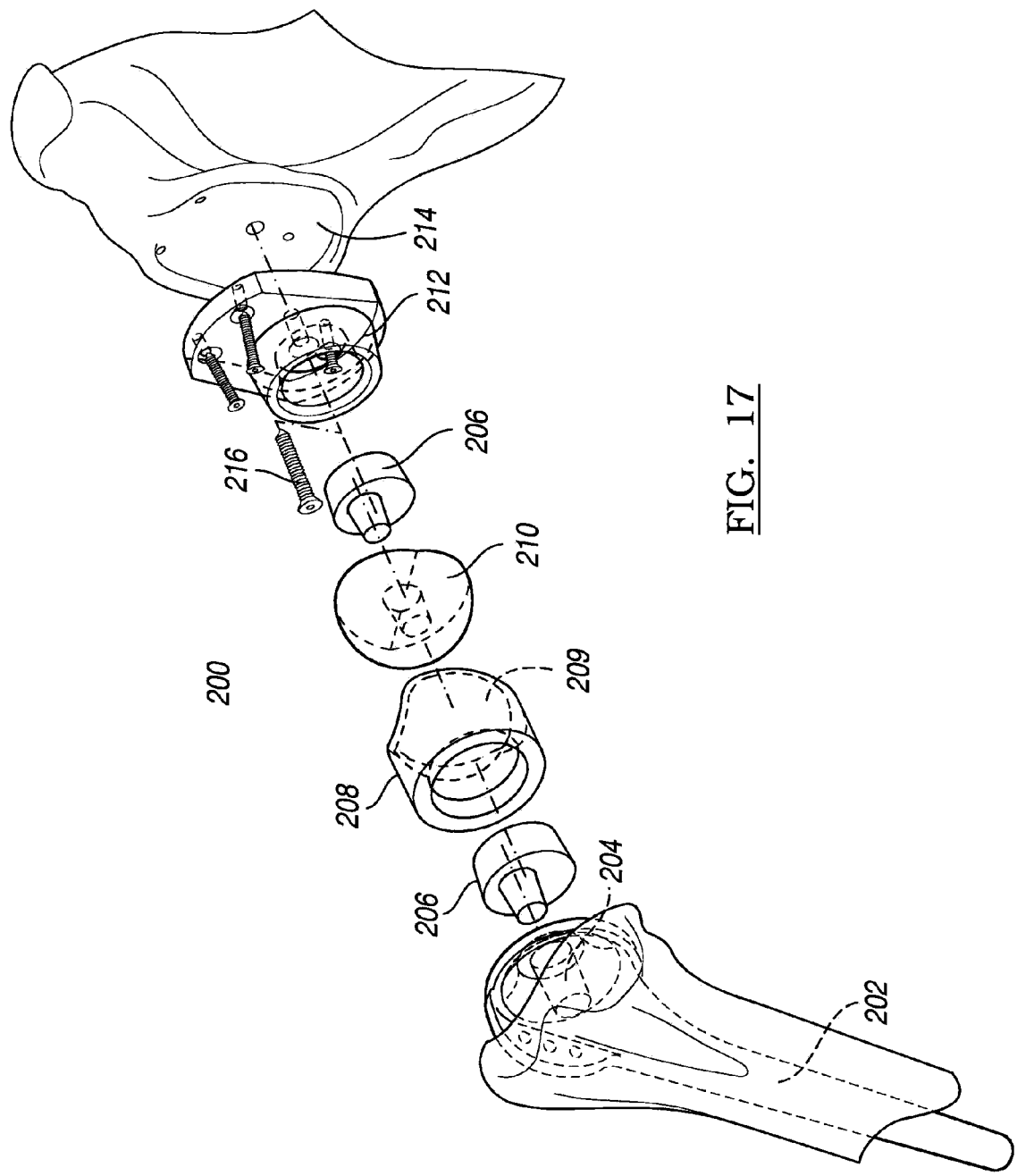
FIG. 17 represents a perspective exploded view of an alternate shoulder prosthetic.

FIG. 17 represents a perspective exploded view of an alternate shoulder prosthetic 200. The prosthetic 200 has a humeral stem 202 which is mated to a bearing 208 that interfaces with a head portion 210. The head portion 210 is coupled to a prepared glenoid 214. The humeral stem 202 has a coupling portion 204 which is configured to mate with a coupling taper 206' on adaptor 206. The adaptor 206 has a coupling taper or taper lock connection 207 which is configured to couple to a corresponding coupling taper 211 disposed on a surface of the bearing 208. The bearing 208 has a bearing surface 209 which articulates with the articulating surface of the head 210.

Figure 18A:
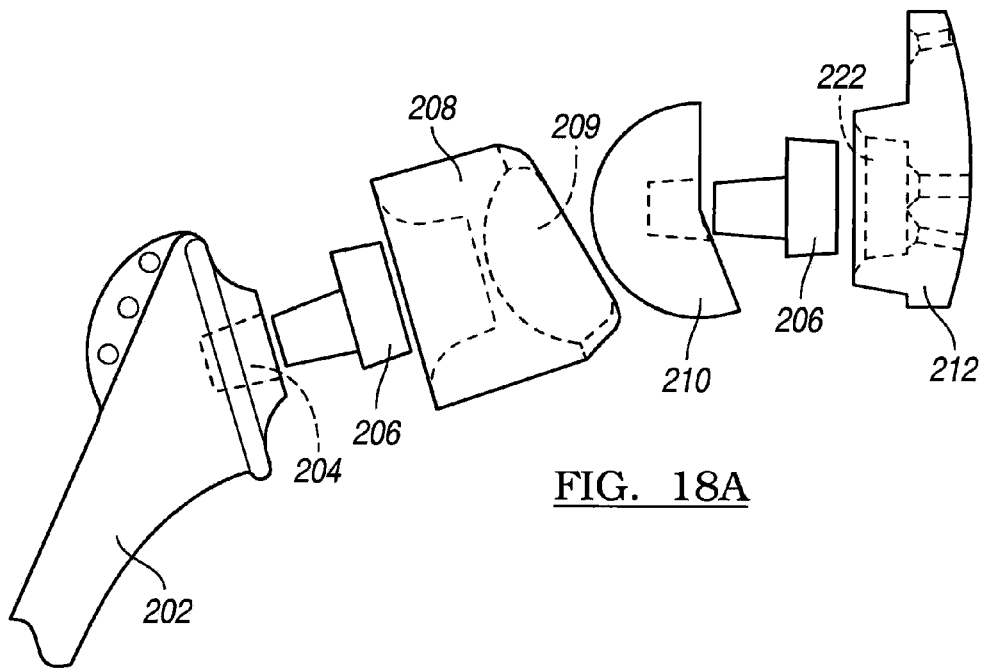
FIGS. 18A-18C represent side views of the shoulder prosthetic shown in FIG. 17.
Figure 18B:
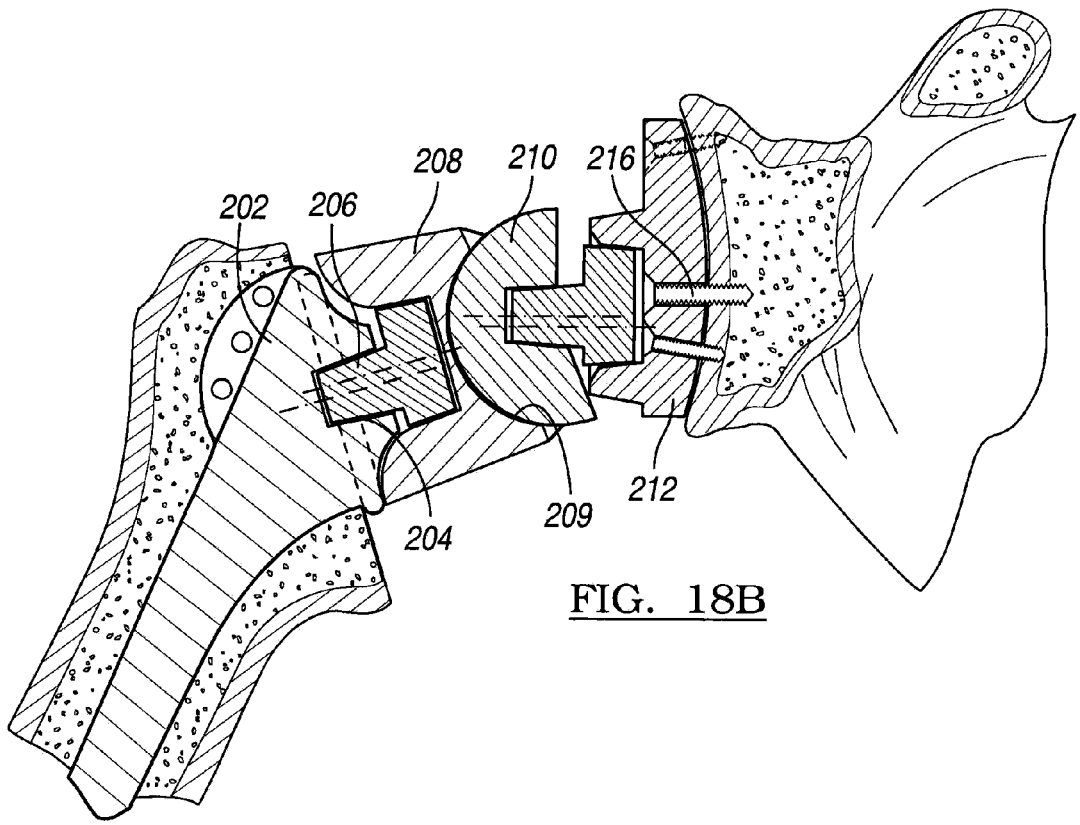
Figure 18C:
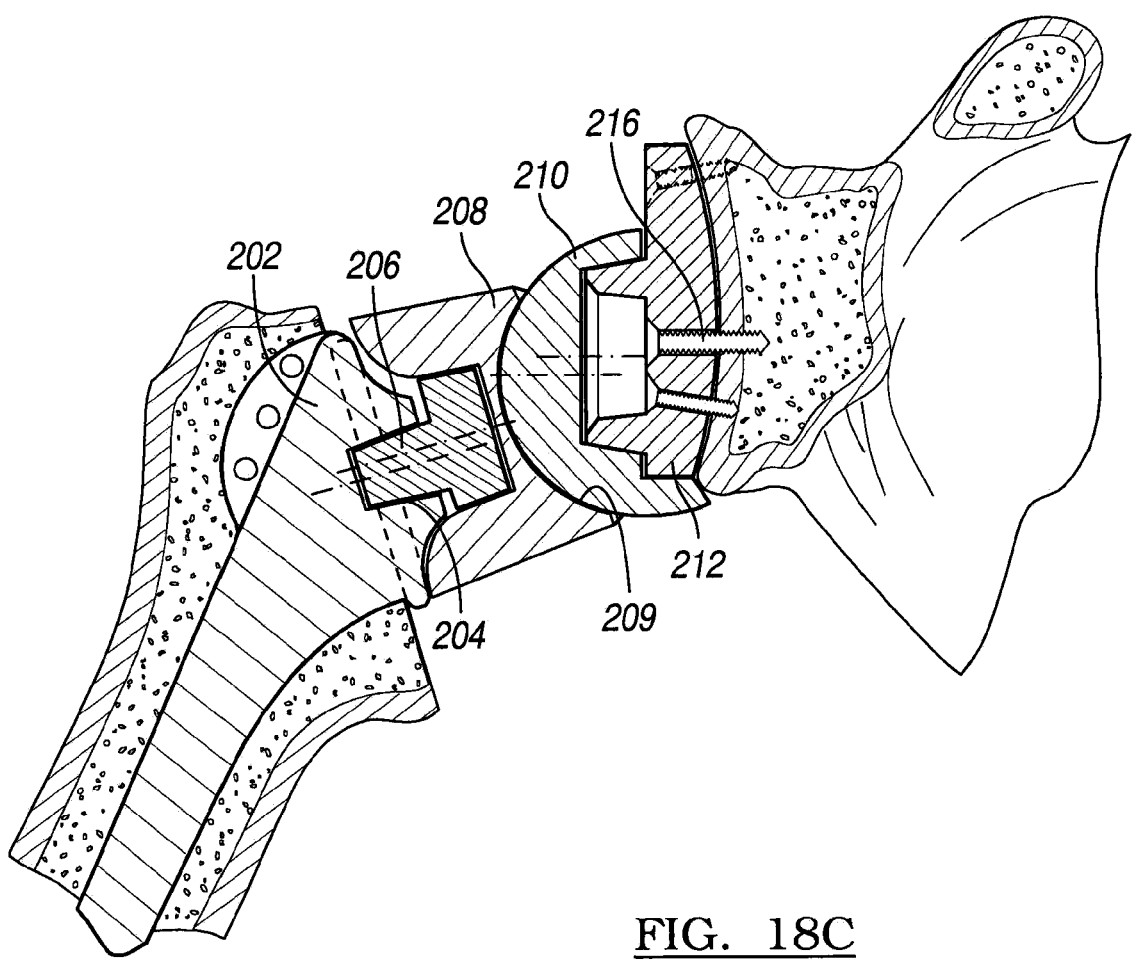

FIGS. 18A and 18B represent a side view of the prosthetic 200 shown in FIG. 17. A second adaptor 206 is disposed between head 210 and the glenoid component 212. The adaptor 206 is configured to interface with a coupling taper 222 defined within the glenoid bearing member 212. It is envisioned the coupling taper 222 can be either a male or a female taper lock connection configured to mate with an appropriate taper on the head 210 (see FIG. 18C).

As shown in FIG. 18B, the glenoid bearing member 212 is coupled to the prepared glenoid 214 using a plurality of fixation screws 216. The adaptors 206 optionally can have a pair of locking tapered members which are off axis from each other, allowing a physician to rotate the offset to align the components within the joint to increase the range of motion of the prosthetic 200. In this regard, the rotation of the adaptors 206 allows for the radial, rotational and angular positioning of the head and cup members. Further it is envisioned that optionally, at least some of the components can be used in a traditional arthroplasty.

Figure 19A:
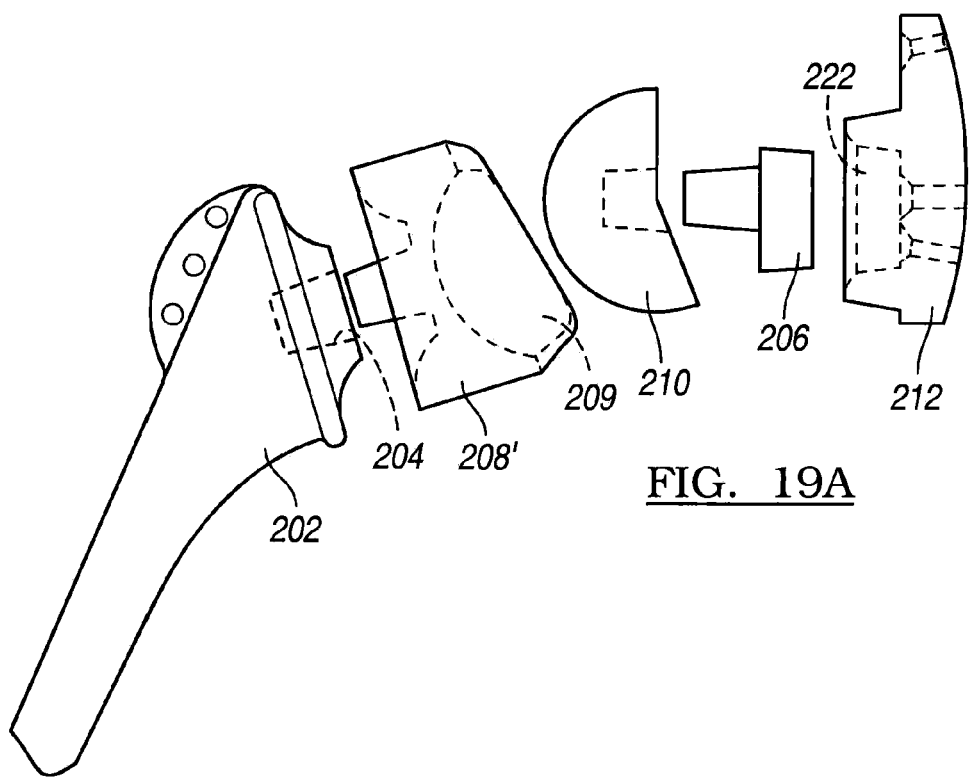
FIGS. 19A and 19B represent side views of an alternate shoulder assembly.
Figure 19B:
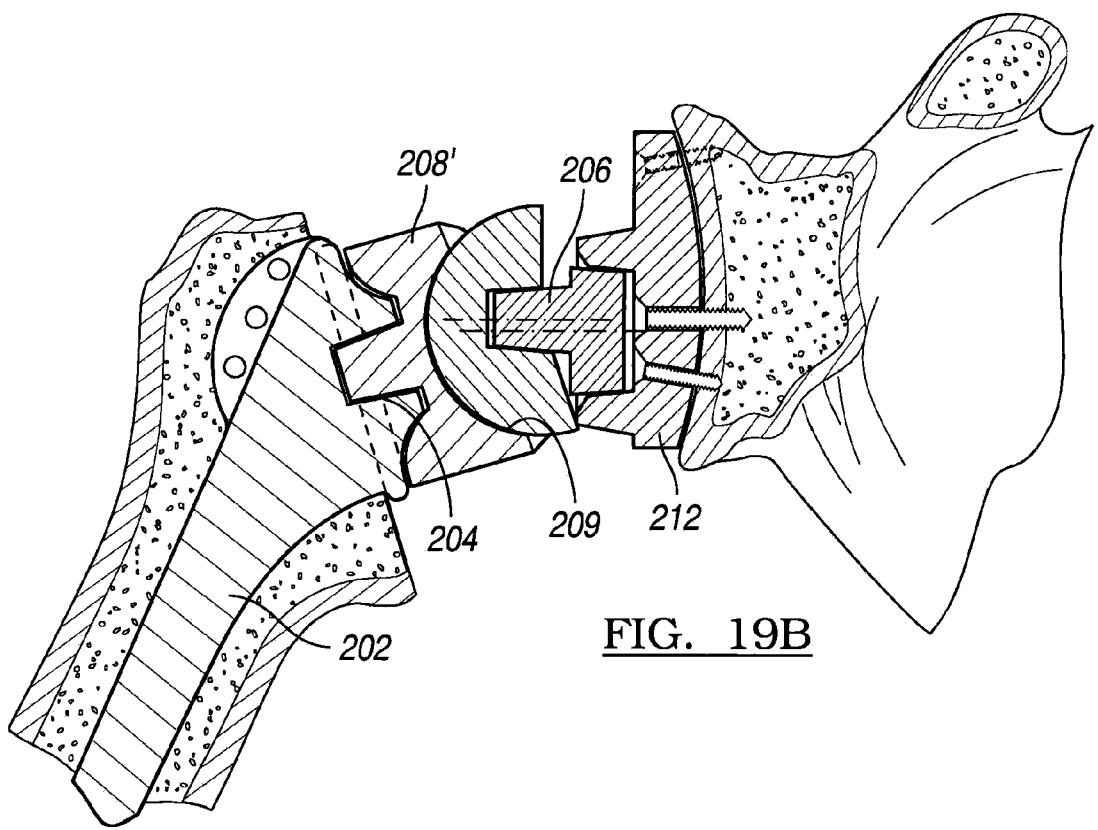

As shown in FIGS. 19A and 19B, the bearing member 208' can be coupled directly to the coupling portion 204 of the humeral stem 202. In this regard, the bearing 208' can have a male coupled taper 206 or a female coupling taper. As shown in FIG. 19B, the use of an adaptor 206 having an offset tapered stem can allow for relative movement of the articulating head 210 with respect to the bearing 208.

Figure 20A:
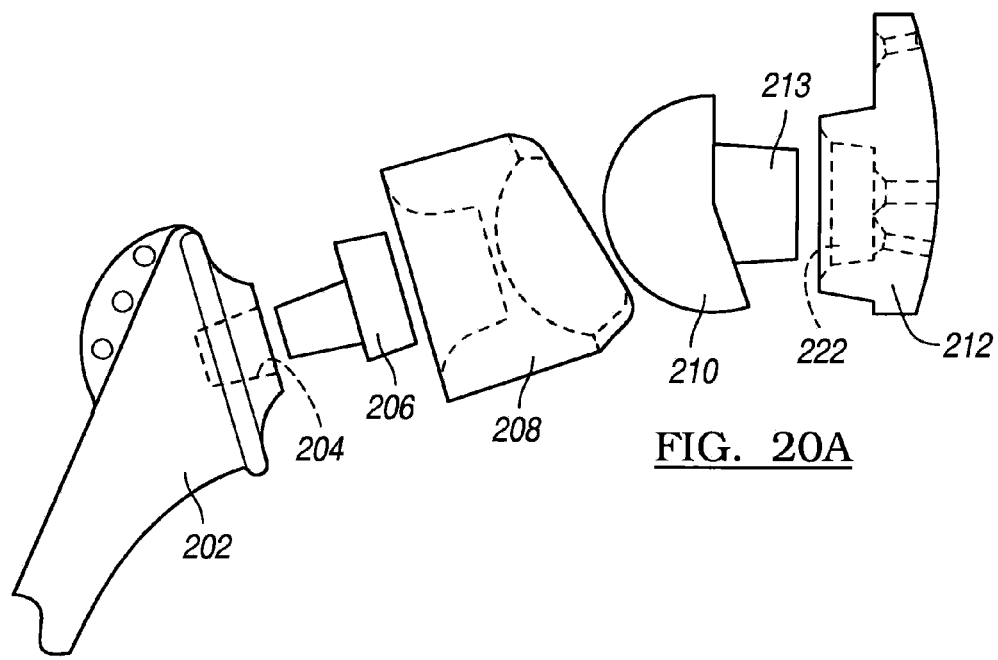
FIGS. 20A and 20B represent side views of an alternate shoulder assembly.
Figure 20B:
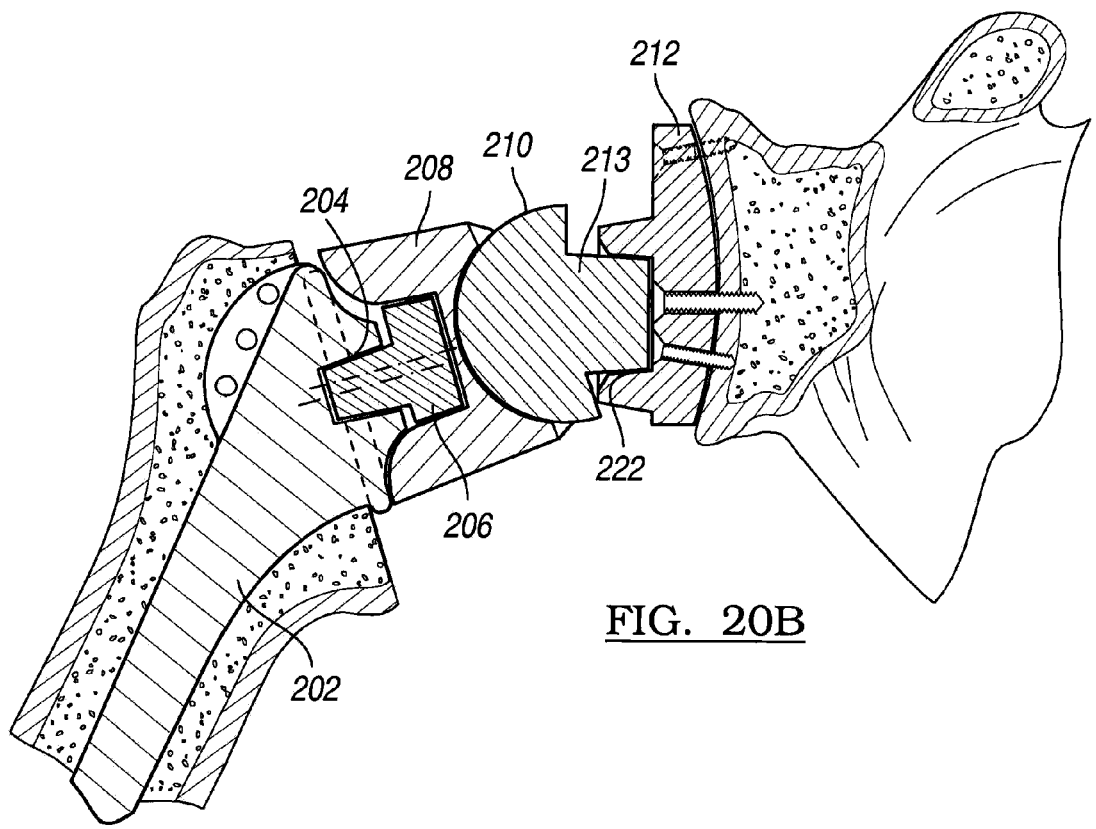

As shown in FIGS. 20A and 20B, the articulating head 210 can have a stem 213 which is configured to couple with a female locking taper 222 within the glenoid component 212. The use of an offset adaptor 206 located between the bearing 208 and the coupling portion 204 of the humeral stem 202 allows for relative displacement of the bearing surface 209 of the bearing member 208 with respect to the head portion 210. Furthermore, by removing the adaptor 206, the size of the joint can be reduced.

Figure 21A:
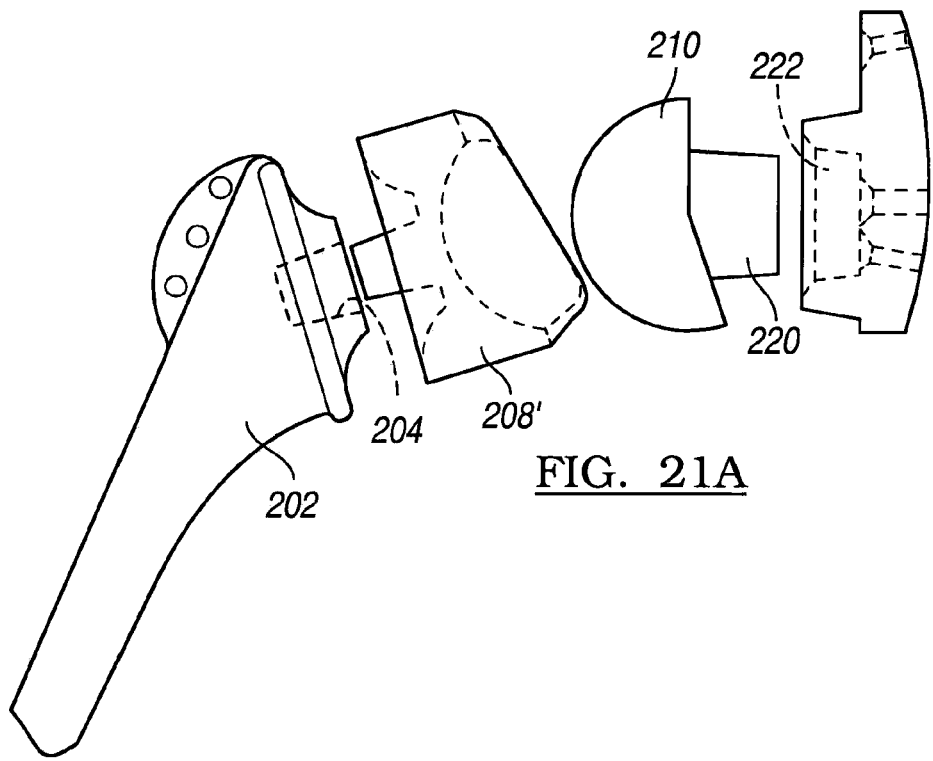
FIGS. 21A and 21B represent side views of an alternate shoulder assembly.
Figure 21B:
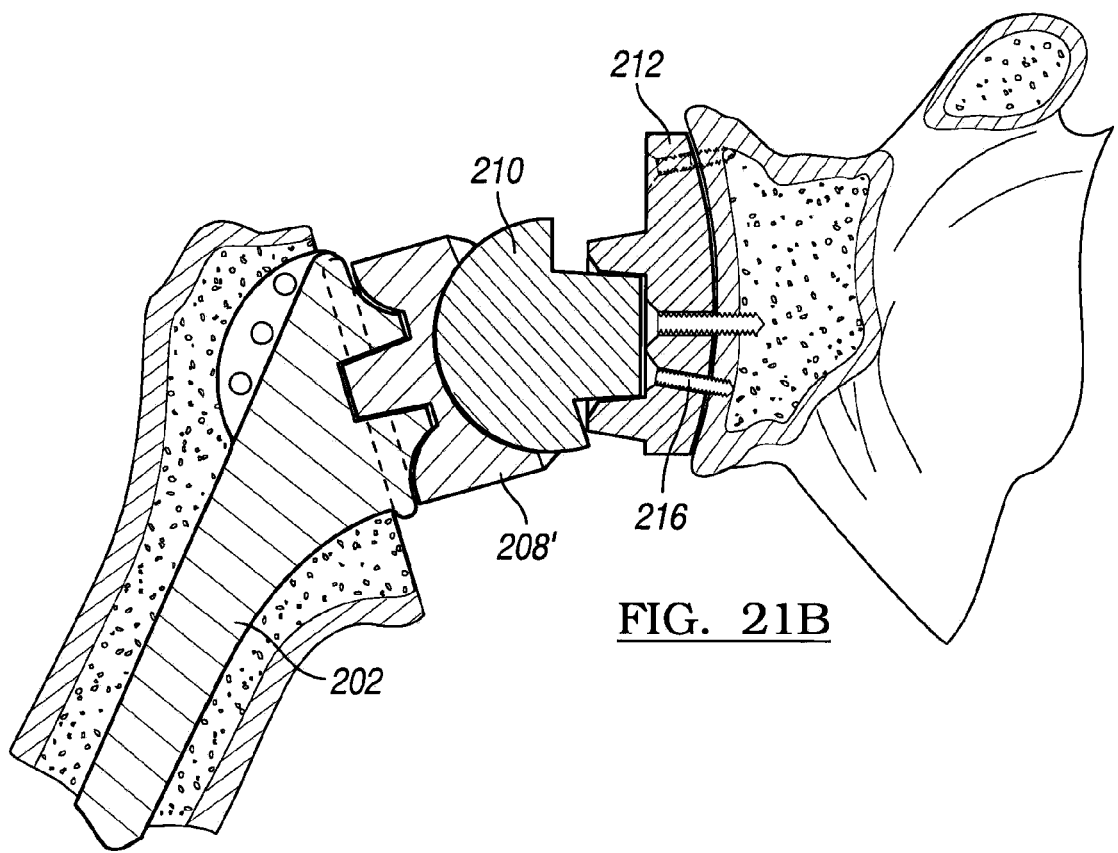

As shown in FIGS. 21A and 21B, the bearing 208 can be directly coupled to a coupling portion 204 of the stem 202. Additionally, the head 210 can be coupled directly to the glenoid component 212 to reduce the overall size of the joint. The direct coupling of the components is accomplished by using locking tapers or fixation members such as threaded fasteners or adhesive.

Figure 22A:
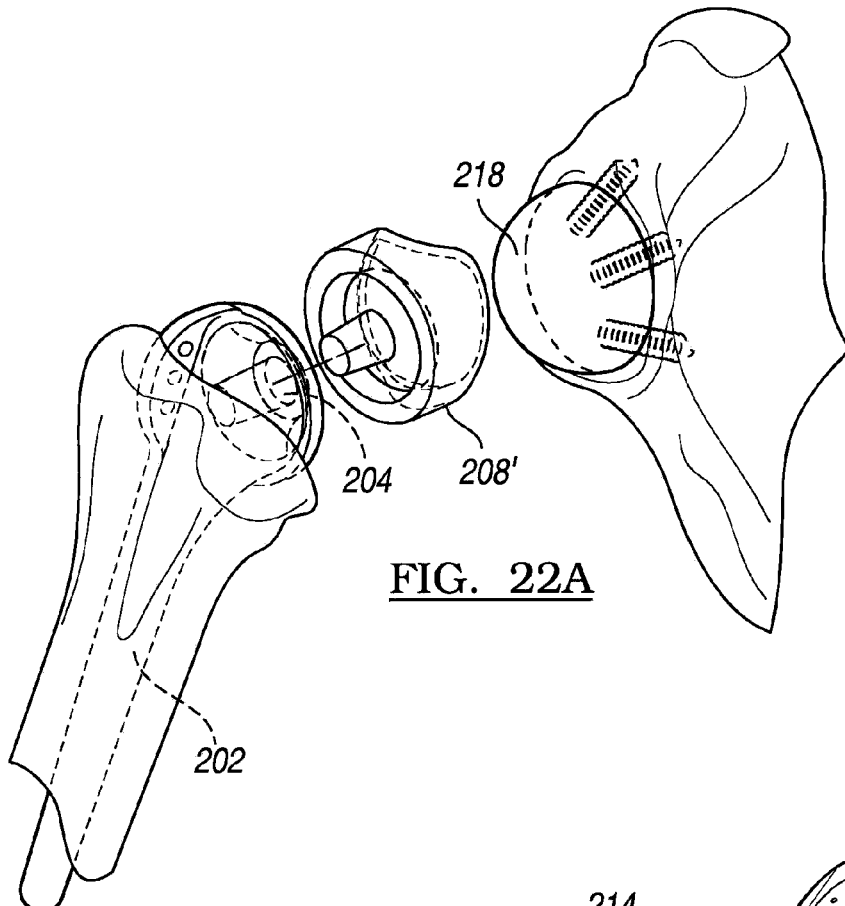
FIGS. 22A and 22B represent side views of an alternate shoulder assembly.
Figure 22B:
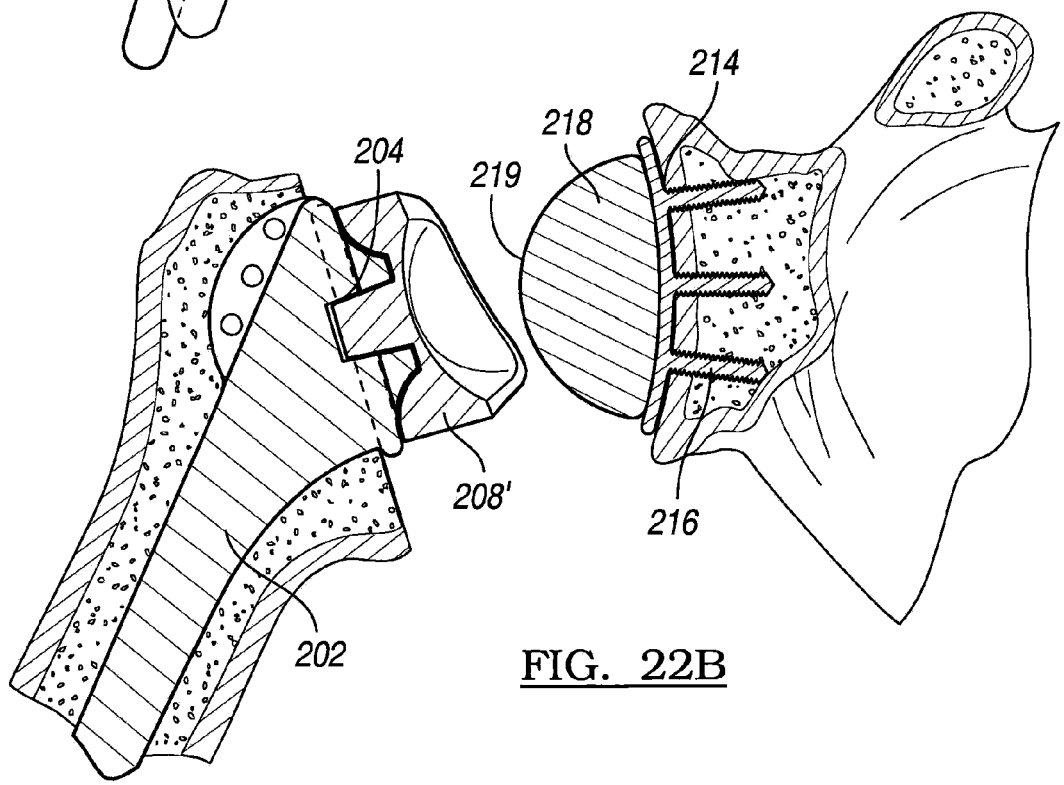

As shown in FIGS. 22A and 22B, a head 218 can be directly coupled to the glenoid 214. This head 218 can be directly coupled to the glenoid 214 using a plurality of bone fixation screws 216 coupled to the head 218. Additionally, an attachment tray (not shown) can be used to couple the head to the prepared glenoid. The bearing surface 219 of the head 218 can have a varying radius of curvature over its surface. In this regard, the radius of curvature can be specifically design to interface with the bearing surface 209 of the bearing member 208 to increase the range of motion while reducing chances of dislocation of the joint.

Figure 23A:
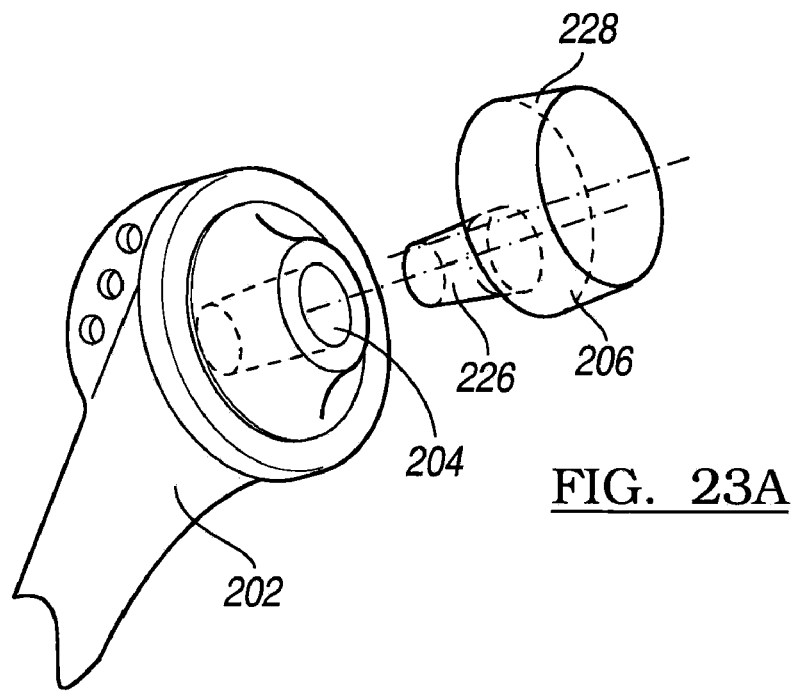
FIGS. 23A and 23B depict the assembly of a humeral component shown in the joint prosthetic shown in FIGS. 20A and 20B.
Figure 23B:
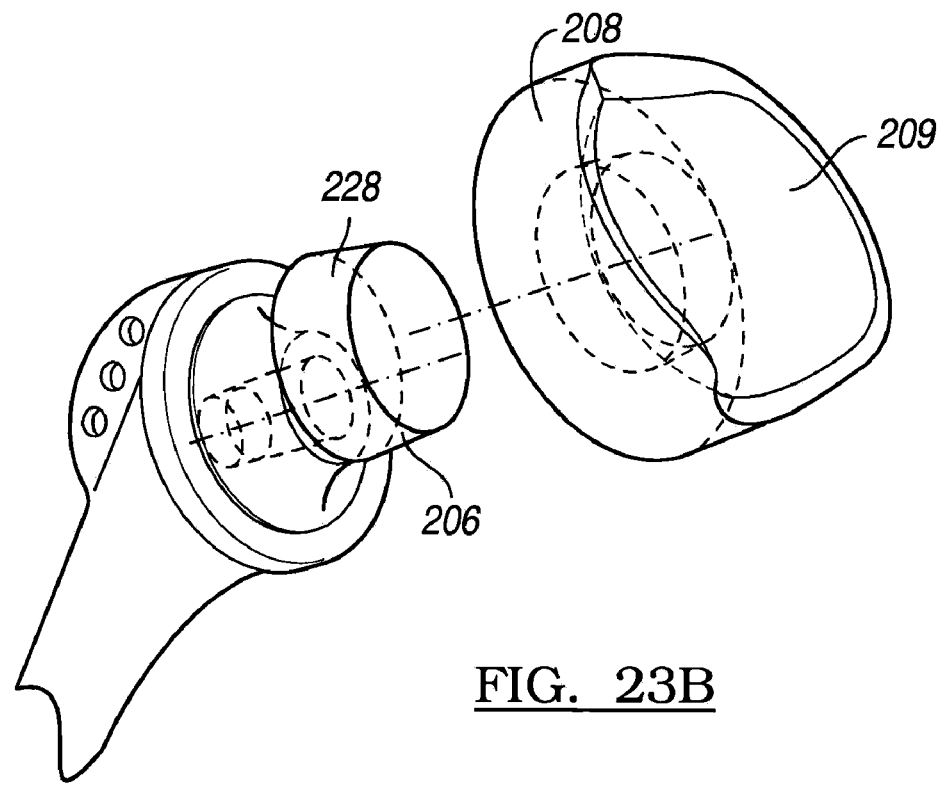
Figure 24A:
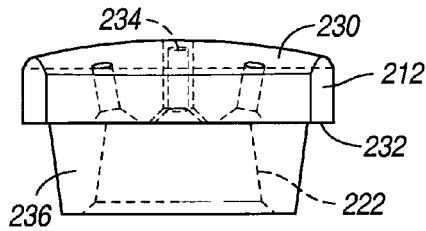
FIGS. 24-26B represent views of the glenoid component shown in FIGS. 17-21B.
Figure 25A:
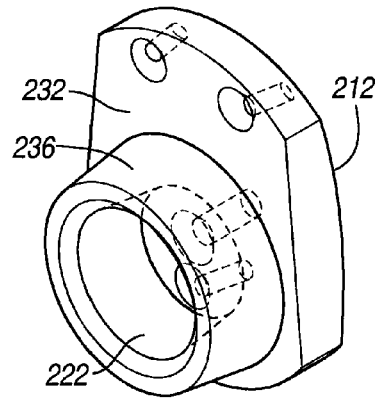
Figure 24B:
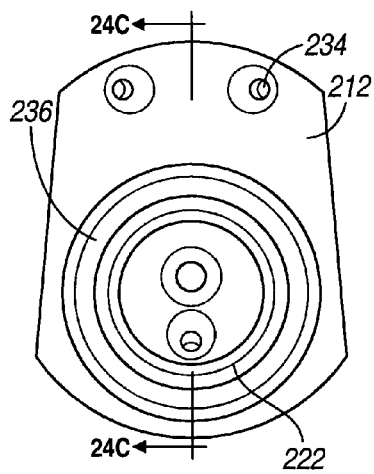
Figure 24C:
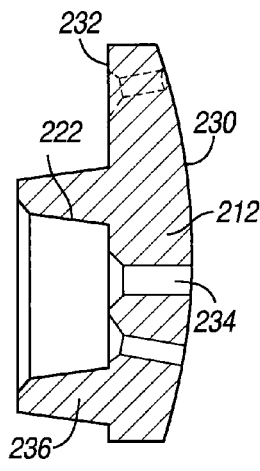
Figure 25B:
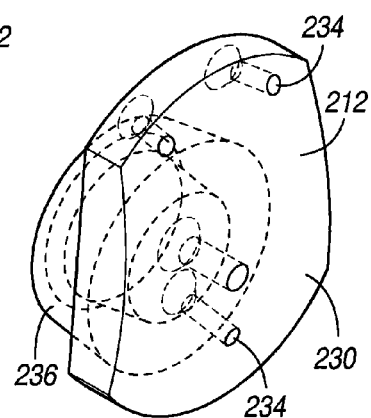
Figure 26A:
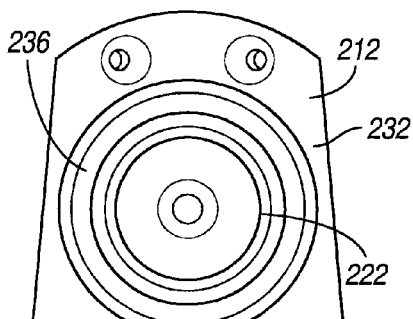
Figure 26B:
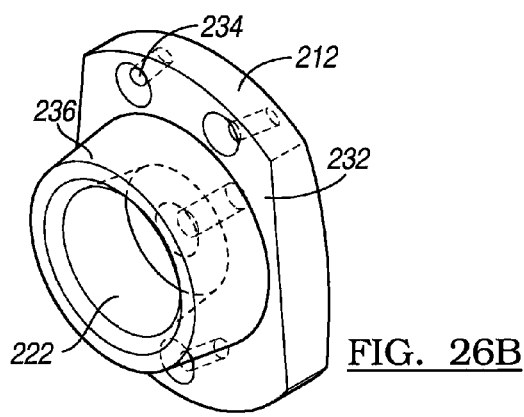
Figure 27A:
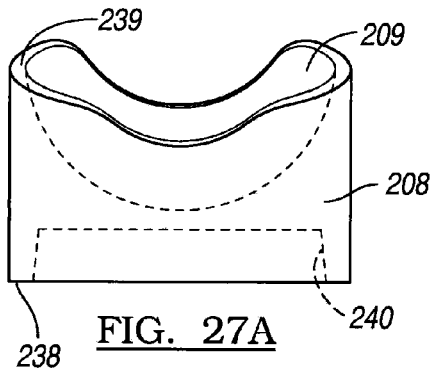
FIGS. 27A-29B represent bearings used in the assemblies shown in FIGS. 18A, 18B, 20A and 20B.
Figure 28A:
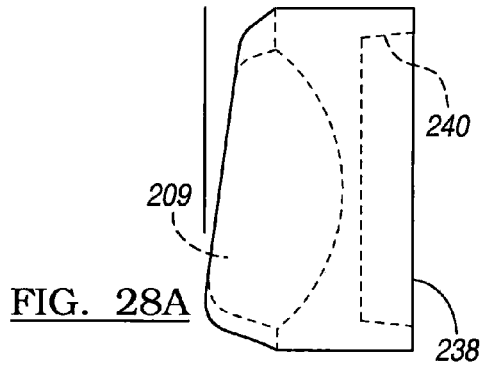
Figure 27B:
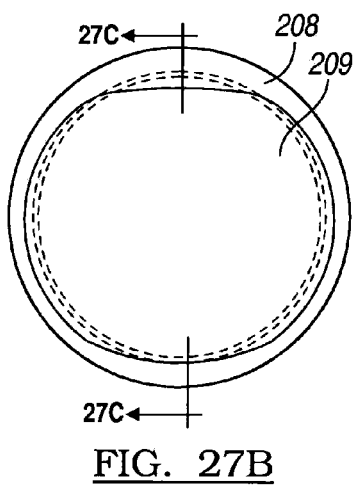
Figure 27C:
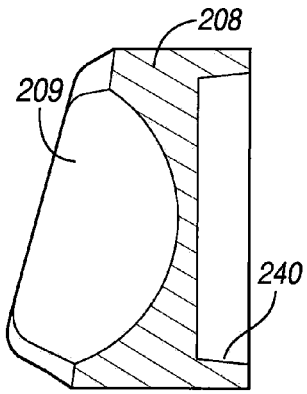
Figure 28B:
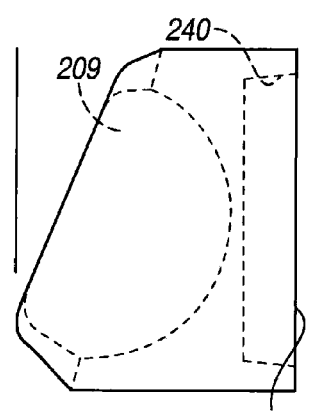
Figure 29A:
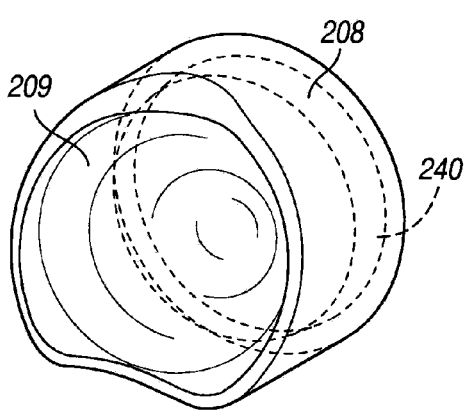
Figure 29B:
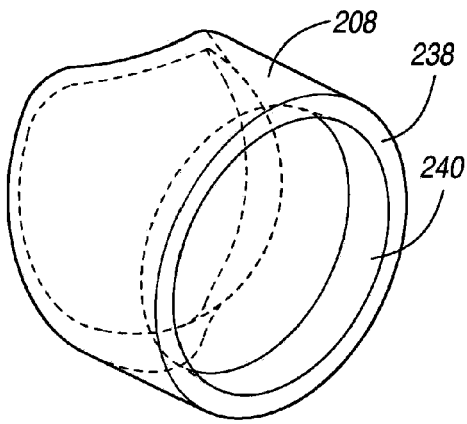
Figure 30A:
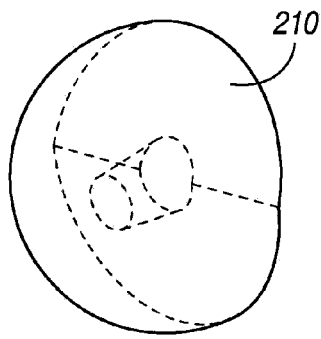
FIGS. 30A-32 represent head components shown in FIGS. 17-22B.
Figure 30B:
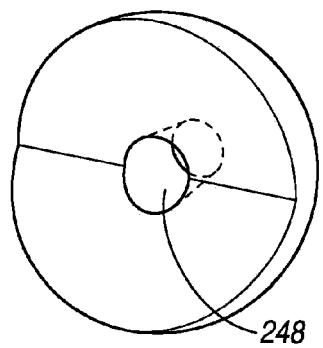
Figure 30C:
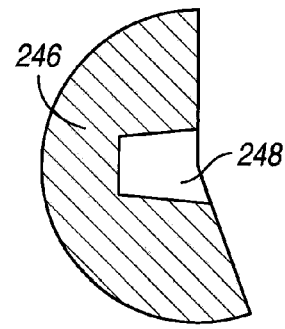
Figure 31A:
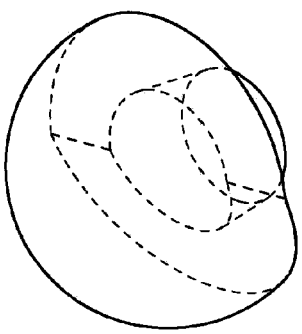
Figure 31B:
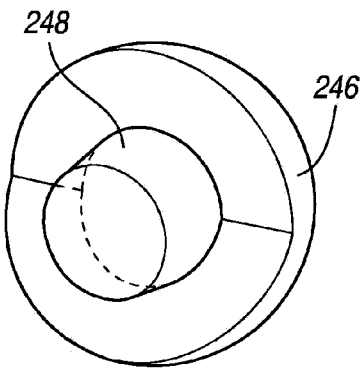
Figure 31C:
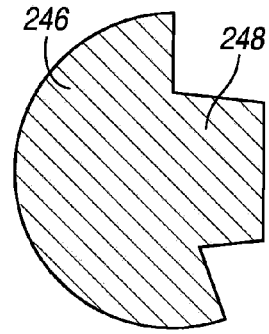

FIGS. 23A and 23B represent the coupling of the bearing member to the humeral component 202. The adaptor 206 is coupled to coupling portion 204 of the stem. In this regard, a male taper lock connection 226 is disposed within the coupling portion 204. The bearing 208 is then coupled to a male taper lock connection 228 disposed on the adaptor 226. A trialing adaptor 206 can be used to allow the placement of the bearing member 208. In this regard, the trailing head is non-fixably coupled to the stem and rotated to place the cup in its proper location. At this point, a regular adaptor 206 is fixably coupled the stem using an impactor as is known.

FIGS. 24A-26B represent alternate views of the glenoid member 212. The glenoid member 212 has a first curved coupling surface 230 which is configured to be mated to a curved surface on the prepared glenoid 214. Additionally, the glenoid 212 has a outward facing surface 232 which is generally opposite to the coupling surface 230. Disposed on the outward surface 232 is a boss portion 236 which defines an exterior fixation taper. Additionally, the boss 236 defines the interior taper 222 which is configured to fixedly accept a male taper of the adaptor 206. Defined through the glenoid component is a plurality of bone fixation holes 234. The bone fixation holes 234 are angled with respect to each other to provide enhanced fixation of the glenoid member 212 to the prepared glenoid 214.

FIGS. 27A-29B represent alternate bearing members 208. Disposed on a coupling surface 238 is the coupling taper 240. The coupling taper 240 is configured to be mated either with an adaptor 206 or with the humeral fixation member 204. Defined on a bearing side 239 of the adaptor 208 is the bearing surface 209. The bearing surface 209 can vary in curvature to maximize the articulation of the head on the bearing surface 208 while minimizing the possibility of dislocation of the head 210 from the bearing 208. As shown in FIGS. 28A and 28B, the surface 209 can have a profile which varies with respect to the bearing side 239 or the coupling surface 238.

Figure 32:
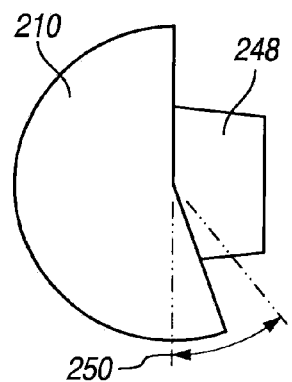

FIGS. 30A-32 represent alternate heads 210 that can optionally be used in the shoulder prosthetic 200. Disposed on a coupling side of the head 210 is a fixation member 248 which can be a female or male coupling taper. As shown in FIG. 32, the head 210 can further have an extended articulating surface 250 which can vary in radius of curvature and in length.

Figure 33A:
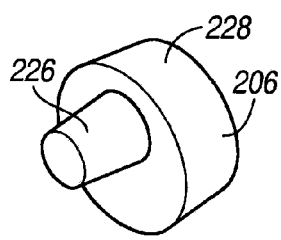
FIGS. 33A-33C represent the adaptor shown in FIGS. 17-23B.
Figure 33B:
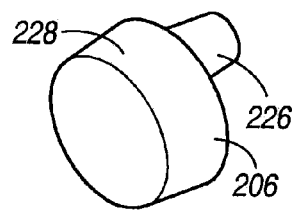
Figure 33C:
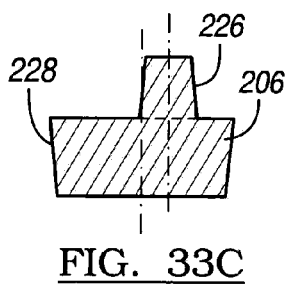
Figure 34:
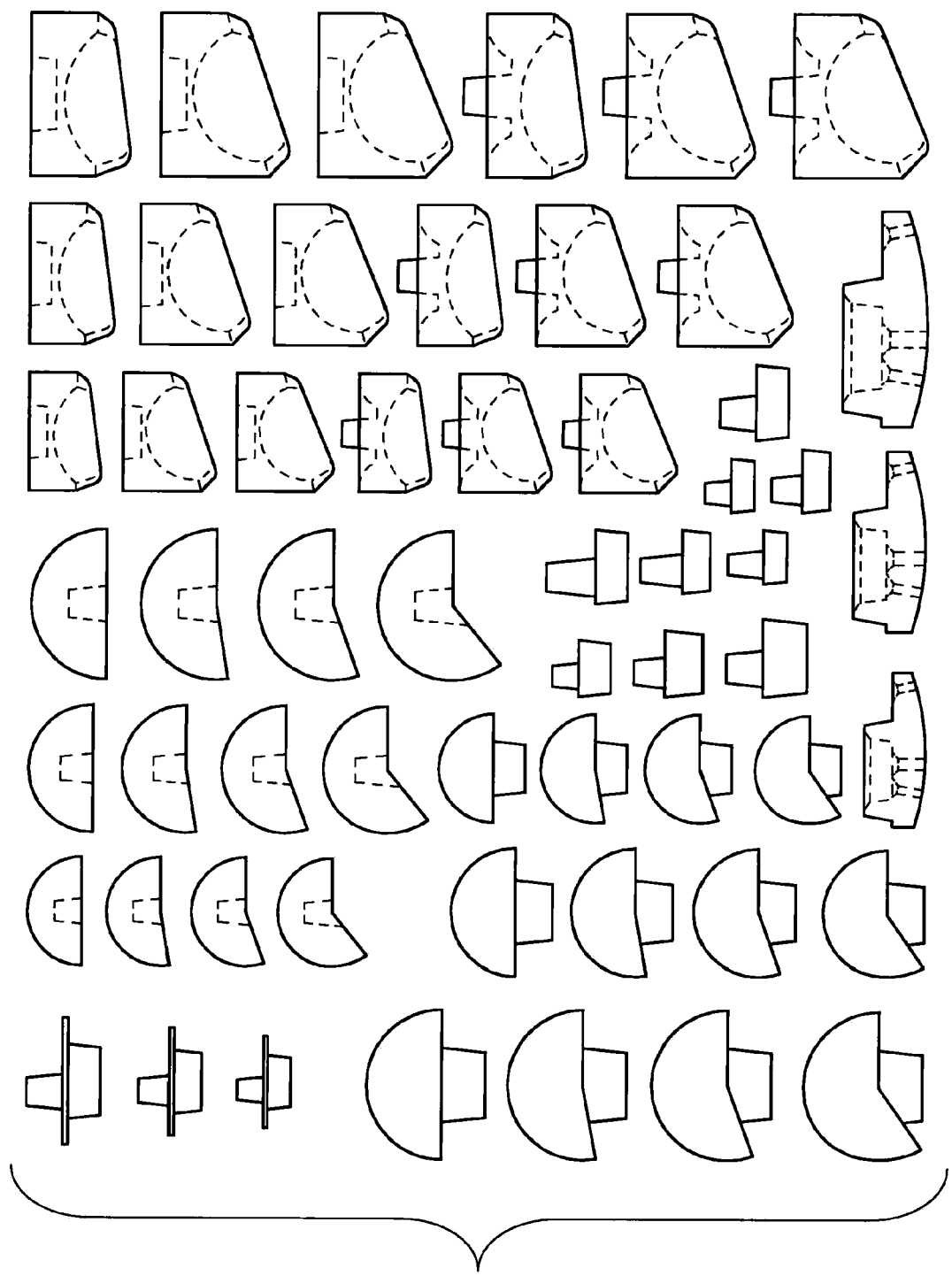
FIG. 34 represents a kit of components shown in FIGS. 17-33.

FIGS. 33A-33C represent adaptors 206 having varying offsets for adjusting the location of the head or bearing member within the joint. It is envisioned the adaptors 206 additionally can have varying heights which allow for varying displacement of the head from the glenoid. FIG. 34 represents the kit of bearing, head, and adaptor members utilized to construct the humeral prosthetic. It is envisioned that this kit can additionally have varying stems and fixation devices such as screws.

Figure 35:
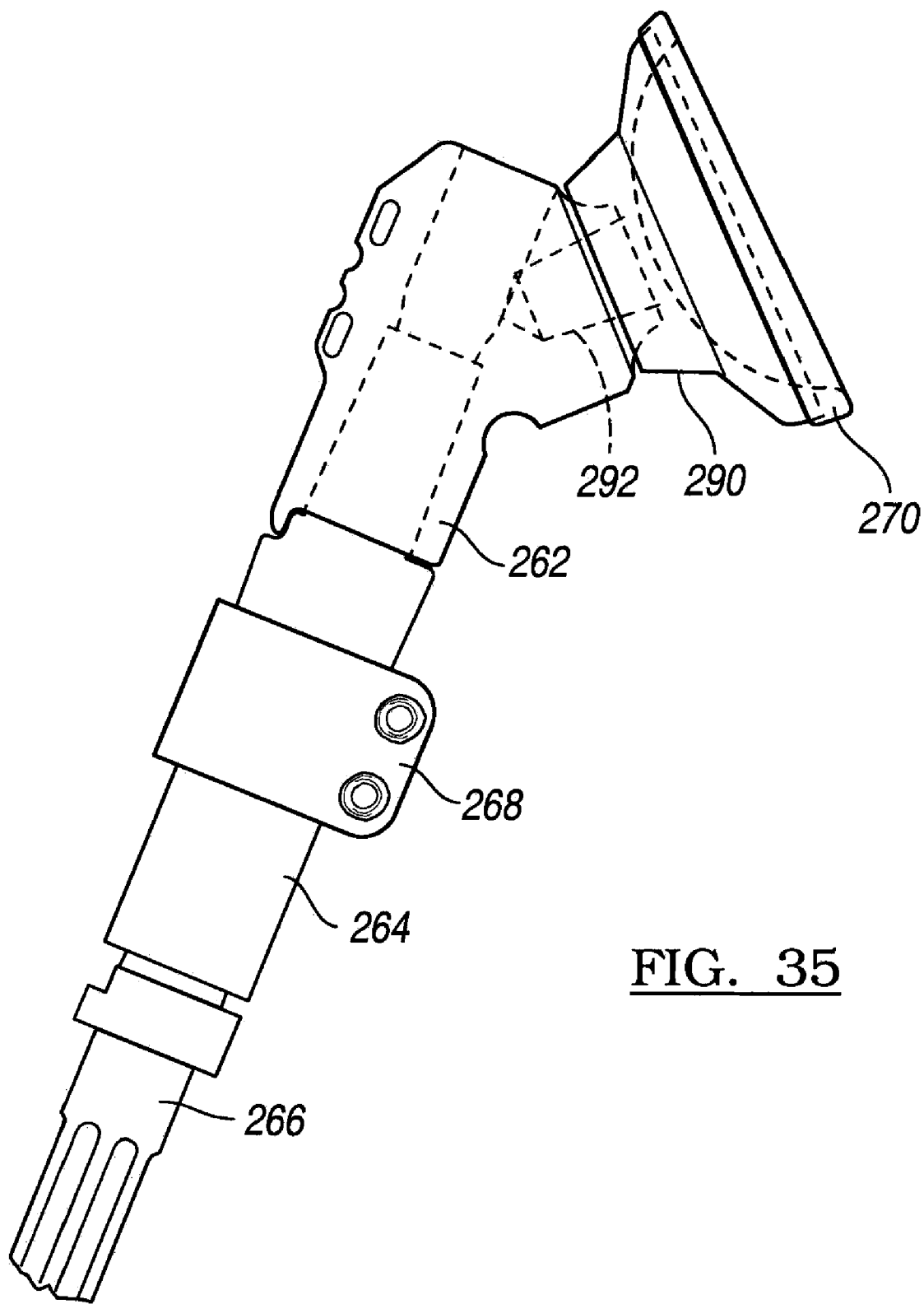
FIG. 35 represents the humeral implant for a reverse shoulder prosthetic.

FIG. 35 represents an alternate reverse humeral prosthetic 260 for use with a large segment humeral resection. The modular humeral prosthetic 260 has a humeral body portion 262, a base member 264, and a fixation stem 266. Optionally, the base member can annularly support a soft tissue fixation member 268. The humeral body portion 262 has a concave bearing surface 270 configured to articulate with a head member in a reverse shoulder. It is envisioned that this concave bearing surface 270 can be a bio-compatible polymer, metal or ceramic. The concave bearing can be coupled to a modular bearing head 290 which is mated with a coupling taper 292 defined in the humeral body portion 262.

Figure 36:
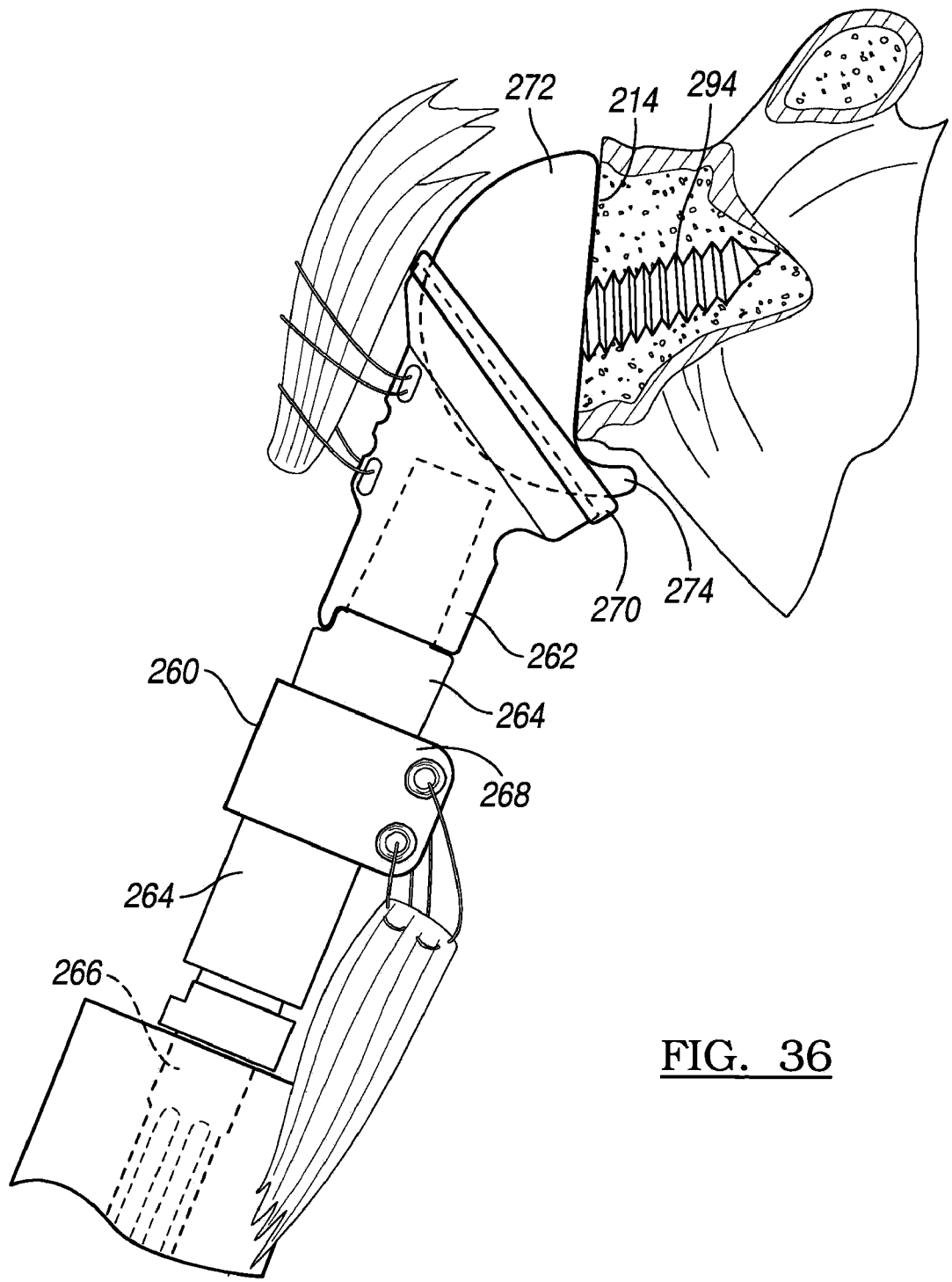
Figure 37:
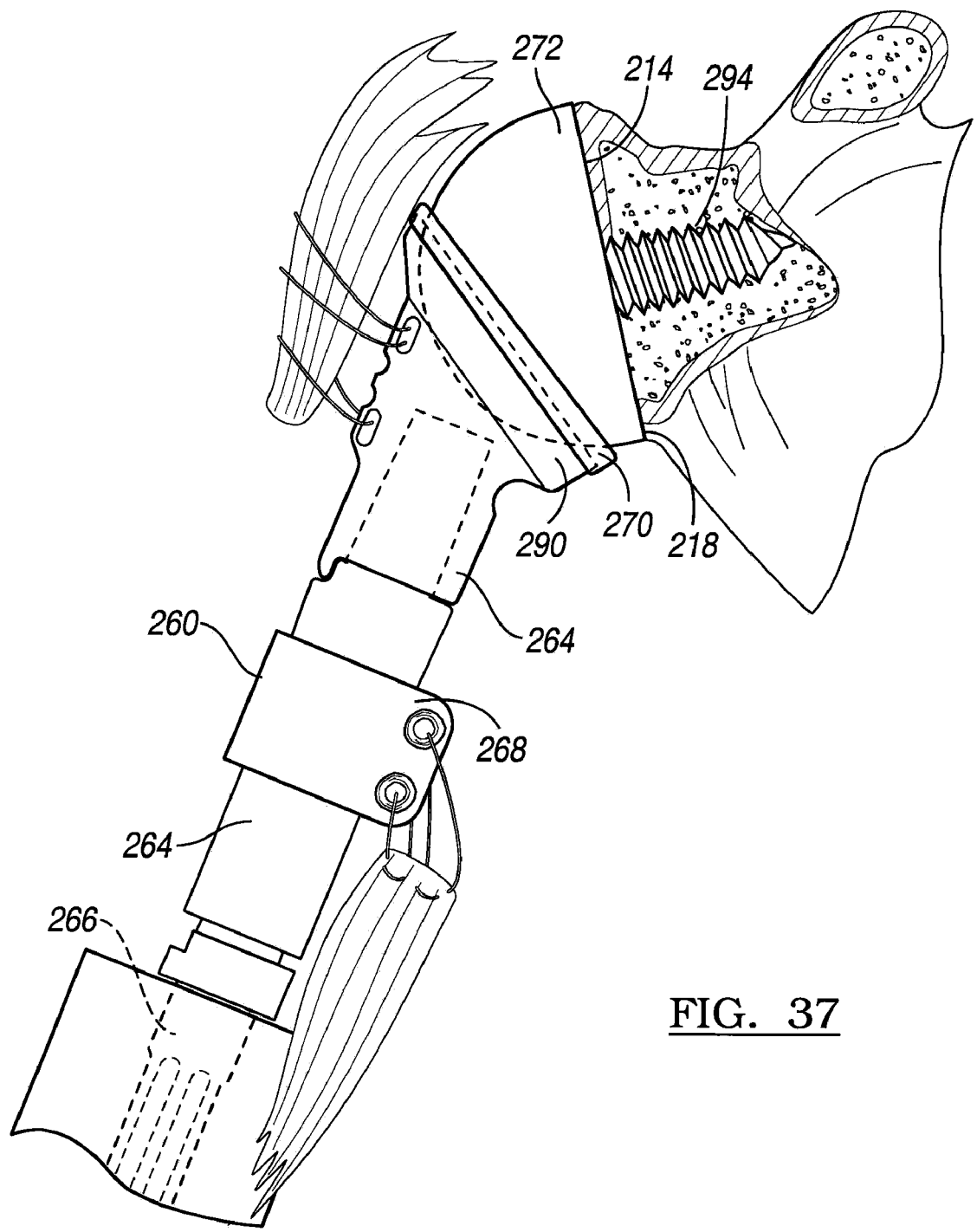
Figure 38:
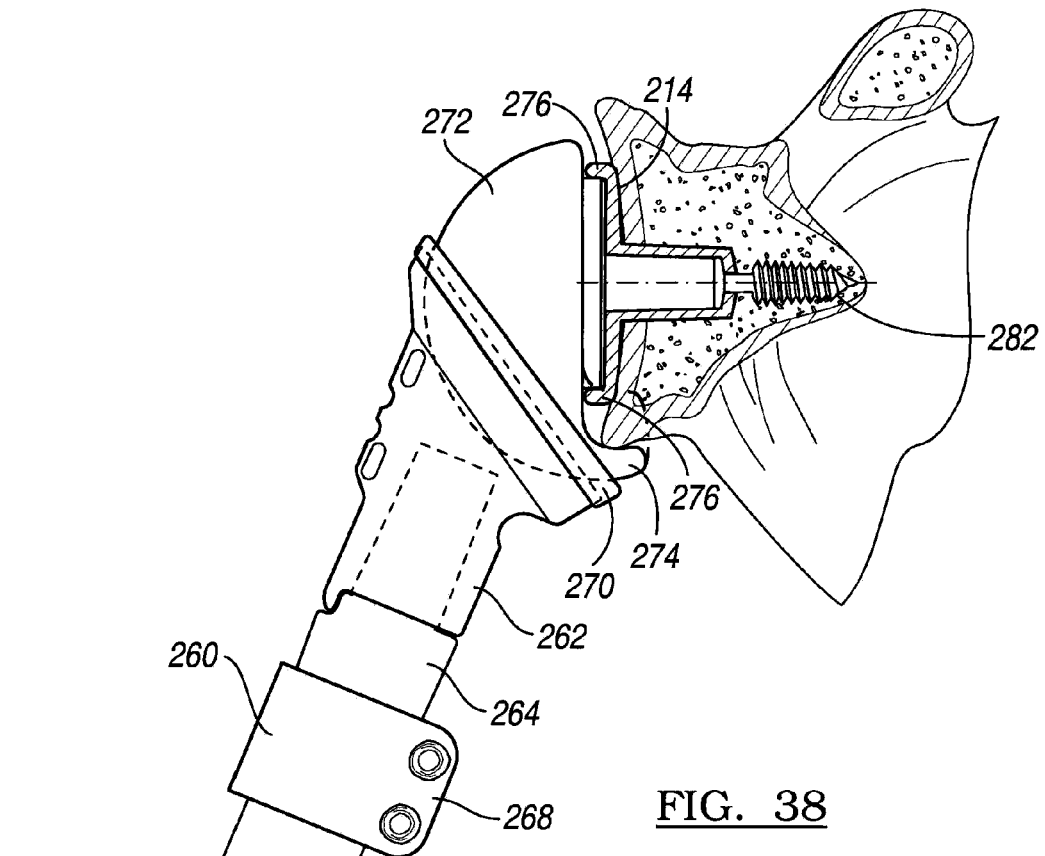

FIGS. 36-38 depict a side view of an implanted humeral prosthetic 260. Each humeral prosthetic 260 is mated with a head 272 that is coupled to the prepared glenoid 214. As shown in FIG. 36, the head 272 of the reverse shoulder prosthetic can be coupled to the prepared glenoid 214 using a large mating screw 294. Additionally, the head 272 can have extended articulating surface 274 to allow for proper articulation of the joint. As FIGS. 36 and 37 represent, the head 272 can have a coupling surface 215 which is generally perpendicular or angled to the fixation screw 294.

FIGS. 38 and 39 represent the coupling of the head portion 272 of the prosthetic to the glenoid 214. Shown is the tray 276 which is inserted into an aperture 277 defined within a coupled glenoid 288. Next, a fixation screw is used to couple the tray 276 to the prepared glenoid 288. A head 272 is oriented and then snapped or fixed to the tray 276.

Figure 41A:
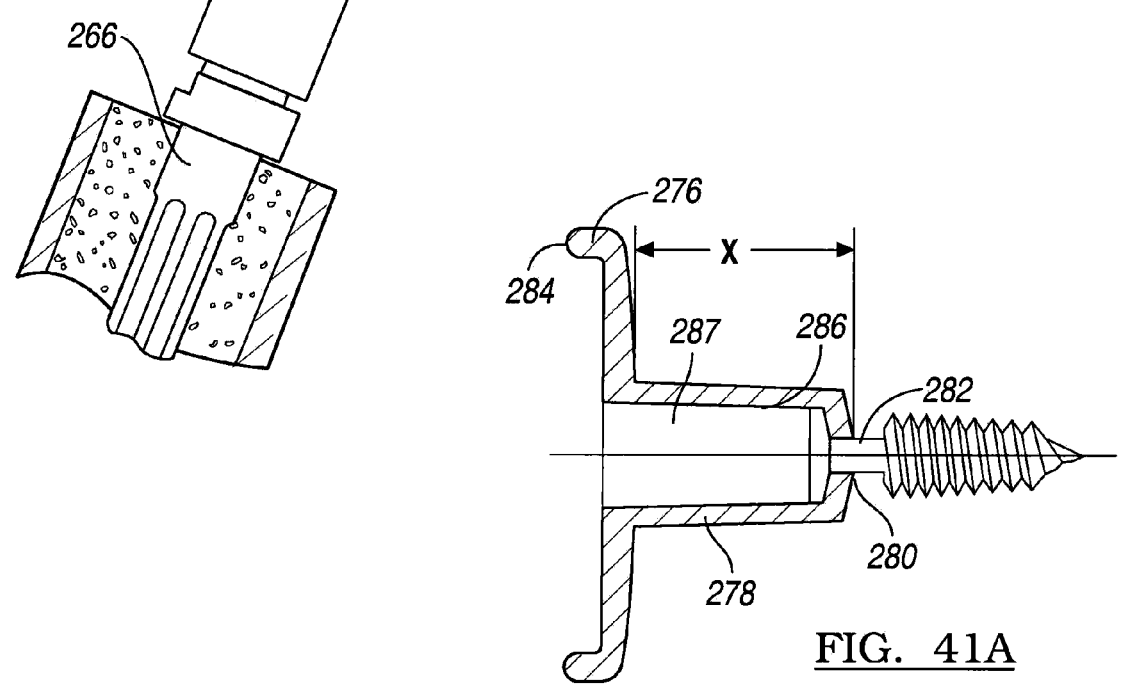
FIGS. 41A-41D represent glenoid fixation components.
Figure 40:
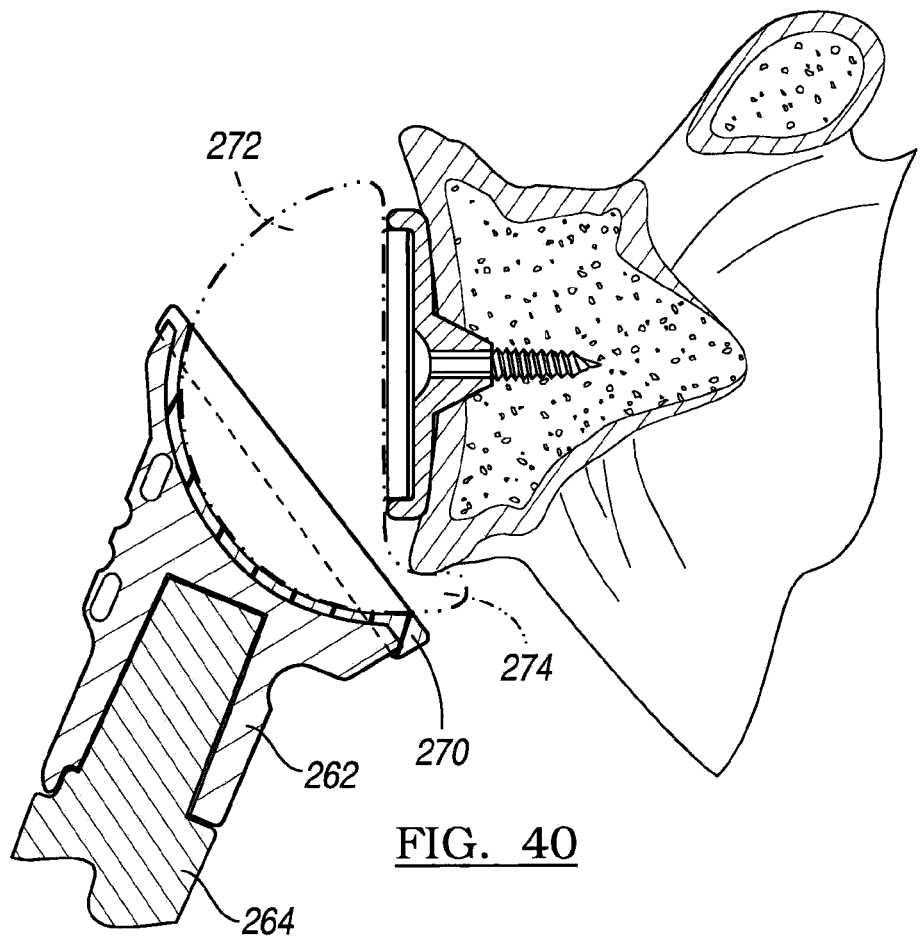
Figure 41D:
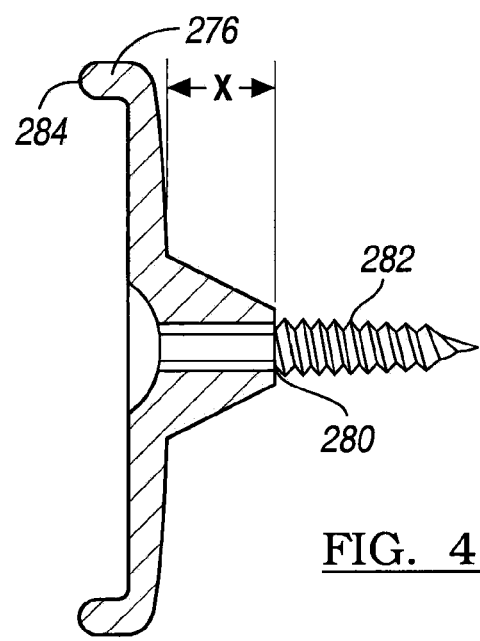
Figure 41B:
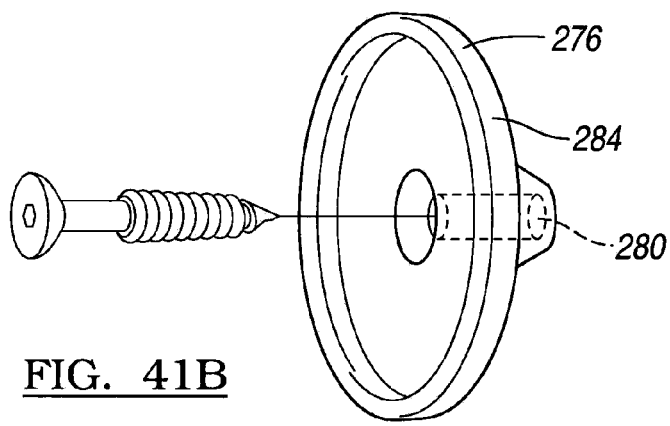
Figure 41C:
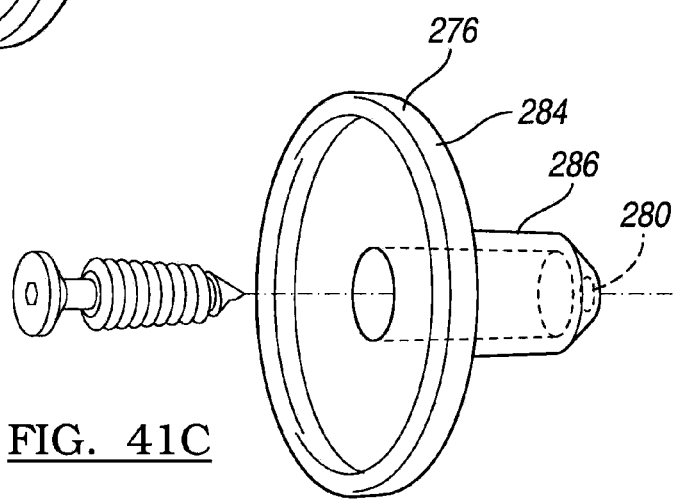

As shown in FIGS. 41B-41D, the tray 276 has a retaining flange 284 and a bone screw accepting aperture 280. Disposed on a coupling surface of the tray 276 is a non-threaded extended region 286 which measures in length greater than 6 millimeters. It has been found that having the extended portion 286 having a length of greater than 6 millimeters allows for the proper coupling of the tray 276 without stress concentration failures in the mating fastener. As shown in FIGS. 41A and 41B, the extended portion 286 can have a counter bore 287, which is configured to accept a head of the bone engaging fastener 282.

Figure 42B:
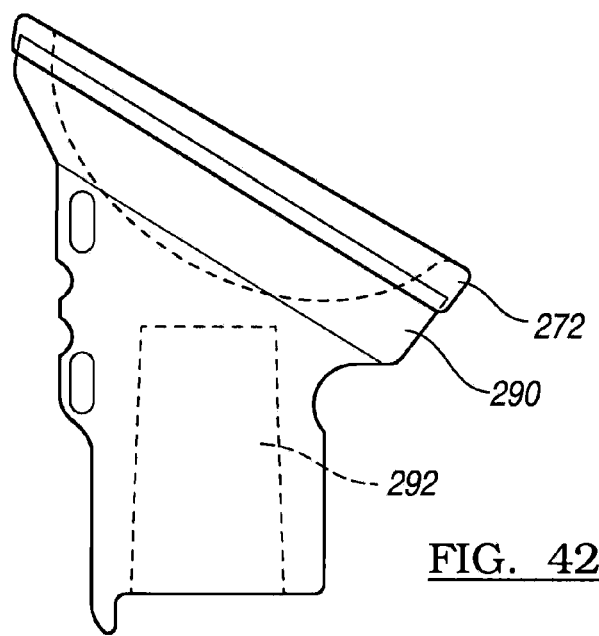

FIGS. 42A and 42B represent the humeral body portion 262. As previously mentioned, the humeral body portion 262 has a concave bearing member 272. The concave bearing member 272 can be integral with the monolithic humeral body portion 262 or may be coupled to a bearing member 290. In this regard, the bearing member 290 can be coupled to a fixation member 294 within the humeral body portion 262. The humeral body portion 262 further has a locking member 292 which can either be a male or female taper to couple the humeral body portion 262 to the base member 264.

Figure 43:
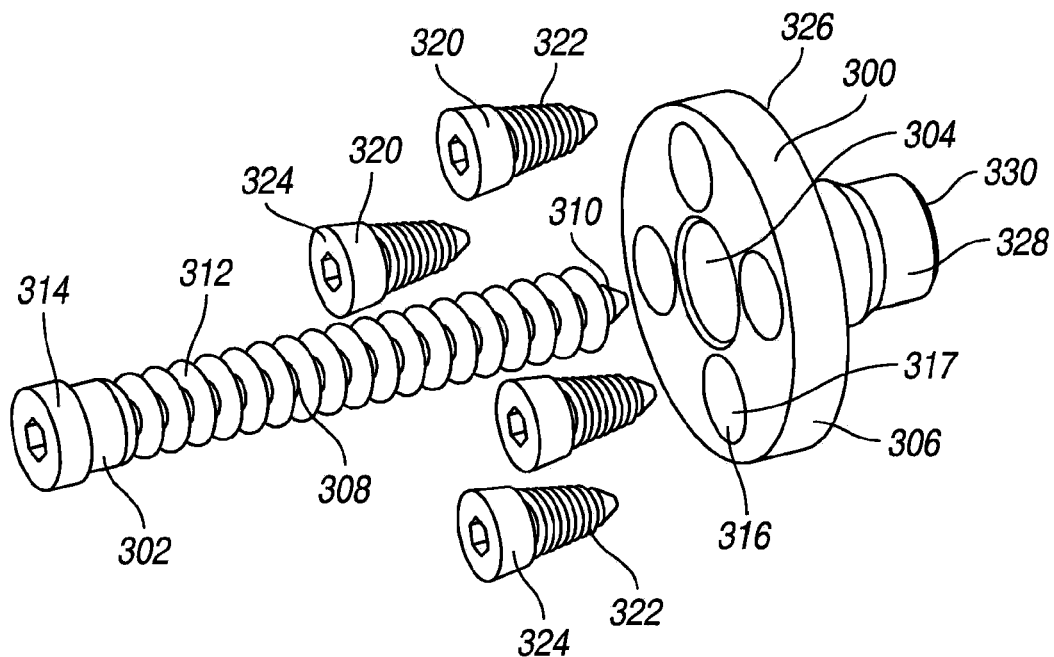
FIG. 43 represents a coupling glenoid tray according to the present teachings.

FIG. 43 represents an alternate tray 300 of the present teachings. Shown is a central fixation screw 302 configured to mate with a central fixation hole 304 defined in a tray plate 306. The central fixation screw 302 has a threaded body 308 having a bone engaging tip 310 and associated coupling screw thread 312. As described below, the screw 302 further has a head 314 configured to be removably coupled to a tray central screw bearing surface 335. Included radially about the central fixation hole 304 are a plurality of bone screw accepting apertures 316. In this regard, four bone screw accepting apertures 316 can have tapered inner surfaces 317 which are defined about the central fixation hole 304.

The screw accepting apertures 316 are configured to optionally accept cortical bone engaging screws 320. The cortical bone engaging screws 320 can have a conical thread exterior surface 322. Associated with the conical exterior surface 322 can be conical heads 324 which are configured to engage a conical inner surface 317 of the screw accepting apertures 316.

The plate tray 306 has a bone engaging surface 326 having a hollow tapered peg 328. As detailed below, the peg 328 defines a through bore 330 linearly aligned with the central fixation hole 304. The tapered peg 328 can have an exterior treatment to enhance the coupling of the hollowed tapered peg 328 with a prepared glenoid 331.

Figure 44A:
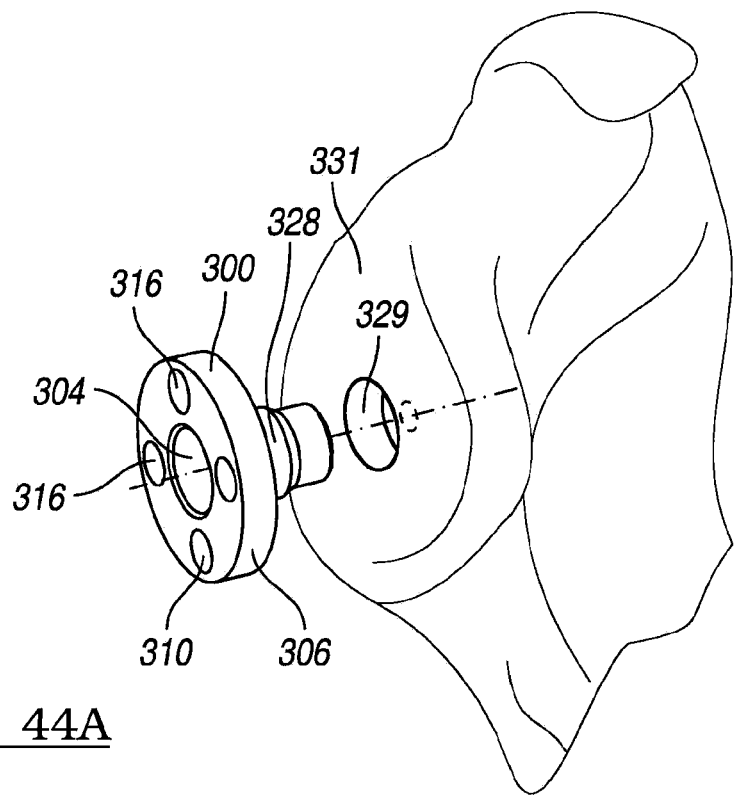
FIGS. 44A and 44B represent the insertion of the tray shown in FIG. 43.
Figure 44B:
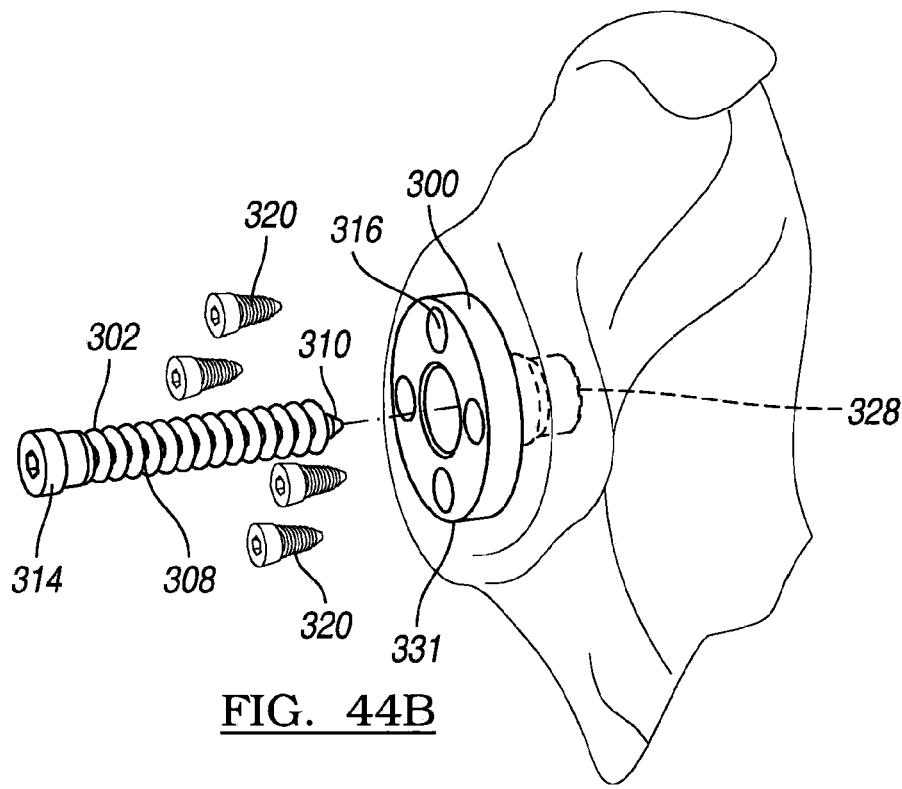

FIGS. 44A and 44B depict the coupling of a tray 300 to a prepared glenoid. As shown in FIG. 44A, an aperture 329 is formed in the prepared glenoid to receive the peg 328. At this point, the tray 300 can be rotated to position the apertures 316 in locations where the bone tissue is most advantageous for coupling of the critical bone screws.

After positioning the peg 328 of the tray 300 in the bore 330, the central fixation screw 302 is passed through the central fixation hole 304 and through the through bore 330 of the hollowed tapered peg 328.

Figure 45:
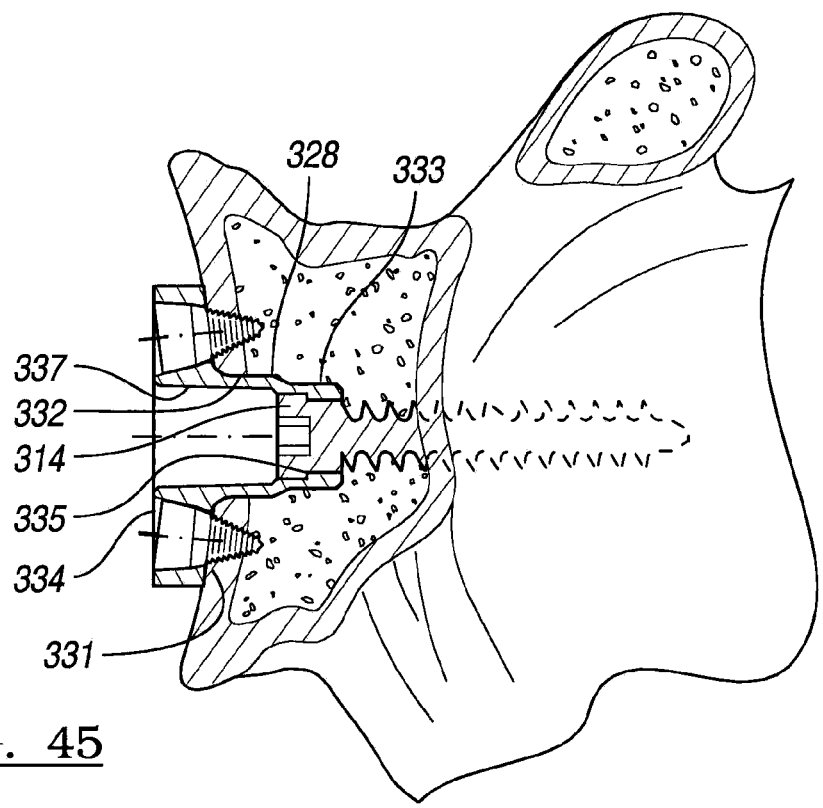
FIG. 45 represents a cross-sectional view of an implanted tray shown in FIG. 43.

As best seen in FIG. 45, the hollow tapered peg 328 has a first portion 332 having a first exterior surface with a first diameter and a second portion 333 having a second diameter smaller than the first diameter. The through bore 330 includes a seat portion 335 configured to function as a bearing surface for engagement with the head 314 of the central screw 302. The location of the seated portion 335 is preferably located about 6 millimeters from the coupling surface 334 of the tray 300. This offset is configured to reduce bending moments and loading on the fixation screw 302. The through bore 330 further includes a coupling interior taper 337 which is configured to engageably receive a corresponding fixation taper 338.

Figure 46:
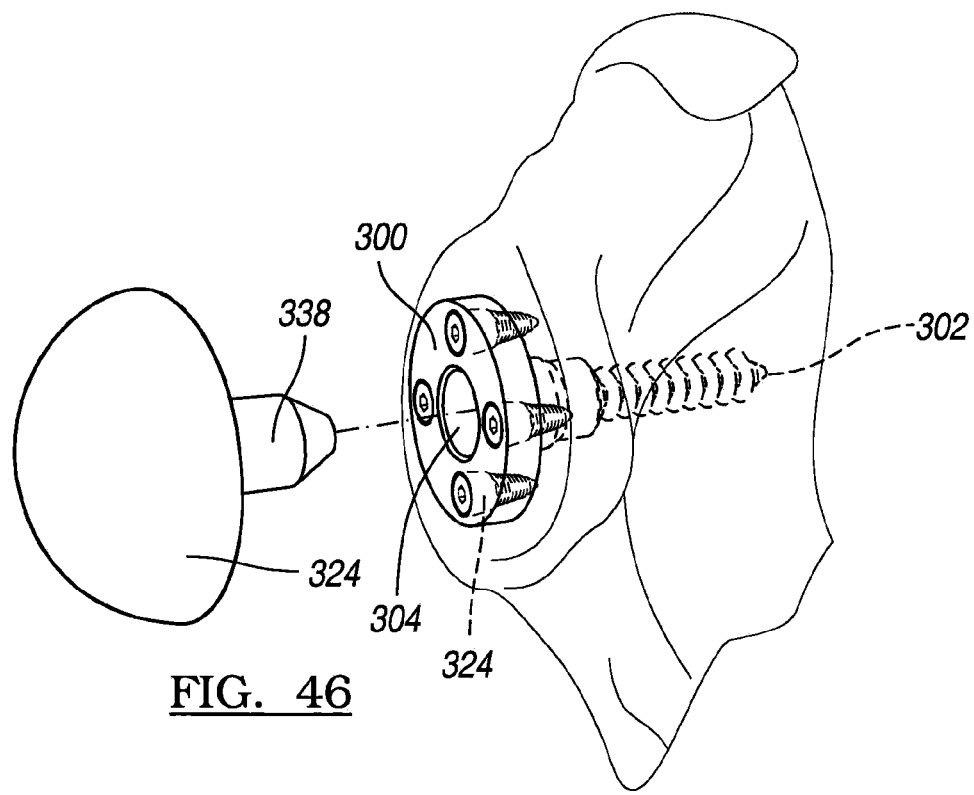
FIG. 46 represents the coupling of an articulating head to the tray shown in FIG. 45.
Figure 47:
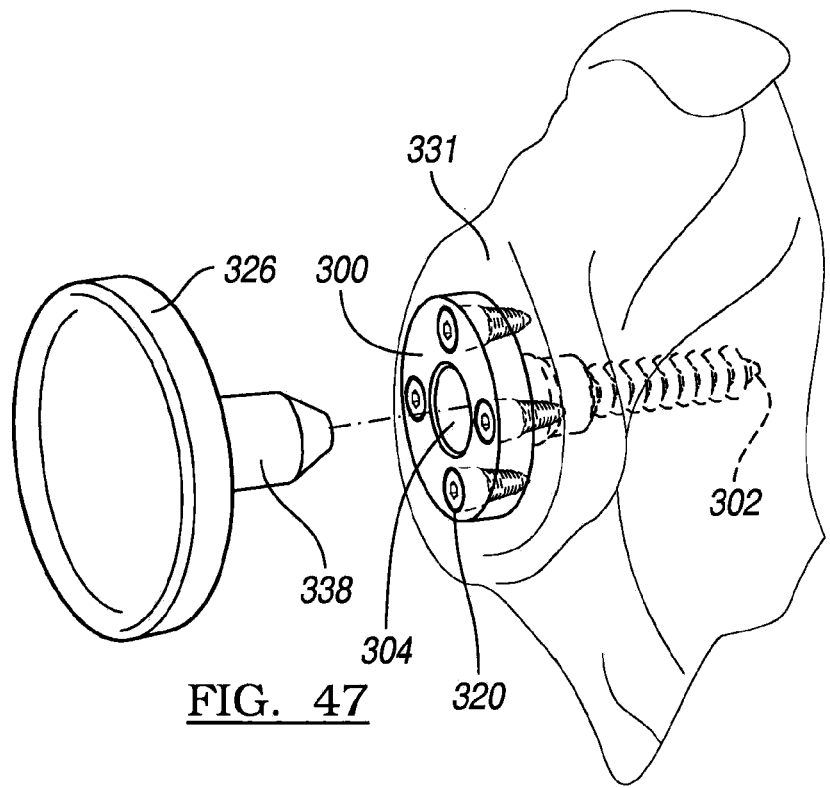
FIG. 47 represents the coupling of a glenoid prosthetic to the tray shown in FIG. 45.

After fixation of the central screw 302, optionally, the plurality of bone engaging screws 320 can be inserted into the bone screw accepting apertures 316. In this regard, the tapered head surfaces 324 of the bone engaging screws 320 can engage the tapered inner surfaces of the bone screw accepting apertures 316. The center lines of the plurality of bone screw accepting apertures 316 may be parallel to the center line of the through bore 330. Additionally, the center line of bone accepting apertures 316 can intersect or skew with respect to the centerline of the through bore 330. As seen in FIGS. 46 and 47, the head 324 or glenoid component 326 can have a male coupling taper 338. The head 324 and glenoid component 326 can have a polymer, ceramic or biocompatible metal articulating surface disposed on a metal support.

As best seen in FIGS. 48 and 49, optionally the tray 300 can be coupled to the prepared glenoid using only the plurality of bone engaging screws 320. In this regard, it is envisioned that the central fixation screws 302 may not be used. In circumstances where the central fixation screw is not to be used, the peg 328 can be solid. Further, the plate can take the form of the plate 170 of FIG. 5 having a plurality of bone screw accepting apertures 316. As shown in FIGS. 50 and 51, a coupling mechanism 330 can be positioned between the head 324 and the tray 300. Optionally, the head 332 can have a countersink 334 configured to encapsulate the tray 300 to place the articulating head 324 close to the resected glenoid.

Figure 52:
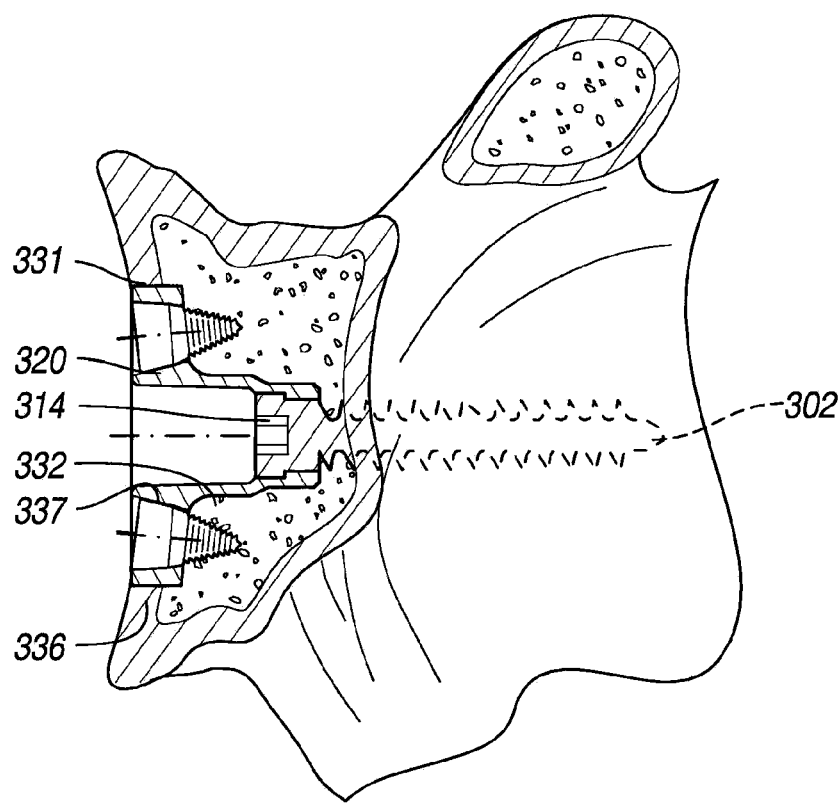
FIG. 52 represents an alternate method of implanting the tray shown in FIG. 43.
Figure 53:
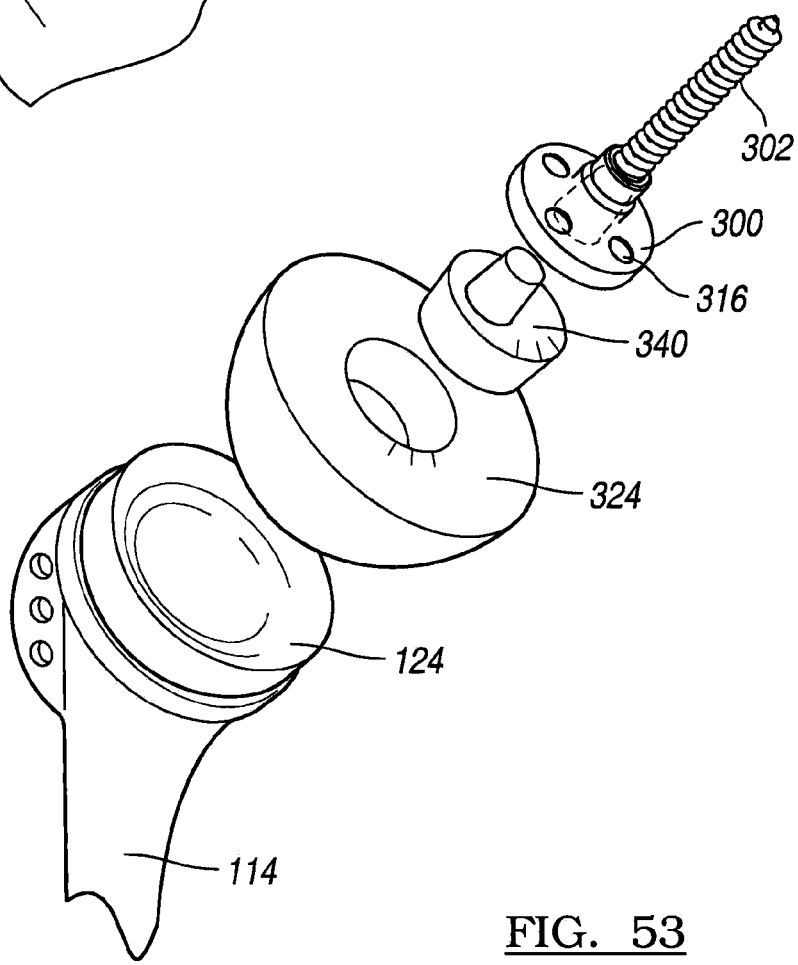
FIG. 53 represents an exploded view of a prosthetic shoulder assembly.

As shown in FIG. 52, the glenoid surface can have a countersink 336 which can encapsulate the plate 306 of tray 300. As shown in FIG. 53, the adaptor 340 can be used to offset a head with respect to the central screw member 302. It is envisioned that this offset adaptor 340 can be used with either a head 324, as shown, or a glenoid component (not shown) to perform either a reverse or regular total shoulder replacement. In this regard, during implantation, any of the aforementioned methods can be used to position a head at the scapula or a cup member. Additionally, previously detailed offsetting intermediate members can be used to change the positions of any of the articulating members within a joint.

Figure 54:
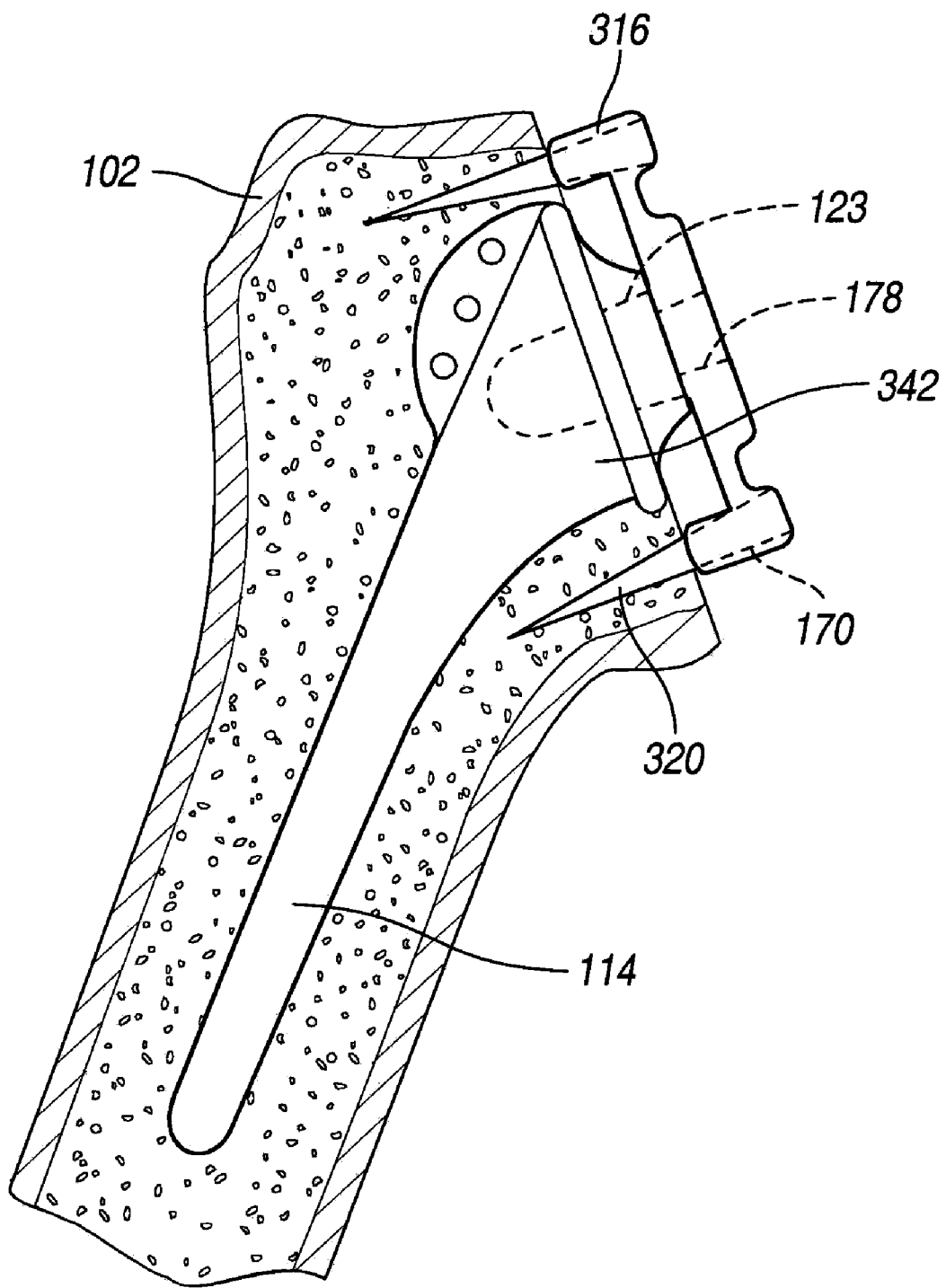
FIG. 54 represent an alternate shoulder prosthesis.

As shown in FIG. 54, a humeral stem 114 can be placed within the medullary canal of a humerus 102. As previously described above, coupled to the female taper 123 of the humeral stem 114 can be the base 170 with corresponding female coupling taper 178. Disposed about a periphery of the coupling taper 178 can be at least one screw accepting aperture 316 which accepts a bone engaging screw or fastener 320. Either the baseplate 170 or the screw accepting aperture 316 can define a fastener head engaging surface. In this regard, after the humeral stem 114 is set into the medullary canal of the humerus 102, the base 170 can be coupled to the female taper 123. Prior to fixably coupling the base 170 to the stem 114, the base 170 can be rotated into position so as to maximize the retention by the bone fixation fastener 320. Fasteners 320 can then be selectively coupled to bone which is radially disposed about the coupling portion 3432 of the stem 114.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiments illustrated by the drawings and described in the specification as the best modes presently contemplated for carrying out this invention, but that the invention will include any embodiments falling within the foregoing description and the appended claims.

What is claimed is:

1. A method for selectively performing reverse and traditional arthroplasty for a shoulder joint that includes a humerus and a glenoid, the method comprising:
   providing a head having a first coupling taper with a first coupling profile, a cup having a second coupling taper with a second coupling profile equal to the first coupling profile and a humeral stem;
   providing a first adaptor with a coupling, said coupling having a peg defining a through bore, said through bore defining a first female coupling taper configured to selectively attach the first coupling taper or second coupling taper to the glenoid, said through bore further defining a screw head bearing surface;
   providing a stem defining a second female coupling taper configured to selectively attach to the first coupling taper or the second coupling taper to the stem;
   coupling the first adaptor to a glenoid;
   coupling a bone engaging screw to the first adaptor after coupling the first adaptor to the glenoid; and
   coupling the cup to one of the humeral stem or the first adaptor, wherein the first and second coupling tapers are configured to be interchangeably coupled to both the first adaptor and the stem.

2. The method of claim 1 further comprising providing a second adaptor configured to couple the head to the humeral stem in traditional arthroplasty.

3. The method of claim 2, wherein one of the first and second adaptor comprises an offset coupling mechanism.

4. The method of claim 1, wherein the head includes a first male taper selectively attachable to one of the humeral stem and the first adaptor.

5. The method of claim 1, wherein the cup includes a second male taper selectively attachable to one of the humeral stem and the first adaptor.

6. The method of claim 1, wherein performing the corresponding arthroplasty includes:
   attaching the head to the first adaptor;
   attaching the cup to the humeral stem; and
   articulating the head with the cup.

7. The method of claim 1, wherein performing the corresponding arthroplasty includes:
   attaching the head to the humeral stem;
   attaching the cup to the glenoid; and
   articulating the head with the cup.

8. The method of claim 1, wherein attaching the first adaptor to the glenoid includes screwing a plurality of bone fixation screws through a plurality of holes defined in the adaptor.

9. The method of claim 1, wherein coupling a bone engaging screw to the first adaptor includes coupling a central screw to the first adaptor through the through bore.

10. The method according to claim 9, wherein coupling the central screw to the first adaptor includes coupling the central screw after coupling the first adaptor to the glenoid.

11. A method for selectively performing a reverse and traditional arthroplasty for a shoulder joint that comprises a humerus and a glenoid, the method comprising:
   determining whether to perform a traditional or a reverse shoulder arthroplasty;
   resecting a portion of a glenoid;
   forming an aperture in the glenoid;
   providing a head having a first locking taper with a first coupling profile, and a cup having a second locking taper having a second coupling profile equal to the first coupling profile;
   placing an adaptor having a peg defining a through bore adjacent to the glenoid, so as to position the peg within the aperture, said through bore defining an adaptor coupling taper;
   placing a bone engaging fastener through the through bore after positioning the peg within the aperture;
   providing a stem having a stem coupling taper; and
   coupling one of the first locking taper for a reverse arthroplasty or the second locking taper for a traditional arthroplasty to the adaptor, wherein the first and second locking tapers are configured to be interchangeably coupled to both the adaptor coupling taper and the stem coupling taper.

12. The method according to claim 11 further comprising coupling a plurality of bone engaging fasteners through a plurality of apertures defined by the adaptor, said apertures being radially positioned about the through bore.

13. The method according to claim 11 wherein the through bore defines a fastener head bearing surface.

* * * * *

UNITED STATES PATENT AND TRADEMARK OFFICE
CERTIFICATE OF CORRECTION

| | | |
|---|---|---|
| PATENT NO. | : 8,070,820 B2 | Page 1 of 1 |
| APPLICATION NO. | : 12/390652 | |
| DATED | : December 6, 2011 | |
| INVENTOR(S) | : Nathan A. Winslow et al. | |

It is certified that error appears in the above-identified patent and that said Letters Patent is hereby corrected as shown below:

Column 3, line 28, "of a assembly" should be -- of an assembly --

Column 3, line 48, "adaptor;" should be -- adaptor, --

Column 4, line 32, "represent" should be -- represents --

Column 6, line 19, "though" should be -- through --

Column 6, line 23, delete "of" after "taper"

Column 6, line 51, "stem humeral 114" should be -- humeral stem 114 --

Column 7, line 4, "humeral stem 123" should be -- humeral stem 114 --

Column 8, line 11, "design" should be -- designed --

Column 8, line 26, insert --to-- after "coupled"

Column 11, line 19, "coupling portion 3432" should be -- coupling portion 204 --

Signed and Sealed this
Twenty-fourth Day of July, 2012

David J. Kappos
*Director of the United States Patent and Trademark Office*